(12) United States Patent
Pepper et al.

(10) Patent No.: US 8,679,276 B2
(45) Date of Patent: *Mar. 25, 2014

(54) NON-COMPLIANT MEDICAL BALLOON

(75) Inventors: Lanny R. Pepper, Larue, TX (US);
Charles J. Cox, Eustace, TX (US);
William F. Davies, Jr., Athens, TX (US)

(73) Assignee: Bard Peripheral Vascular, Inc., Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/616,219

(22) Filed: Sep. 14, 2012

(65) Prior Publication Data

US 2013/0048200 A1 Feb. 28, 2013

Related U.S. Application Data

(63) Continuation of application No. 12/537,995, filed on Aug. 7, 2009, now Pat. No. 8,313,601, which is a continuation-in-part of application No. 12/187,259, filed on Aug. 6, 2008, now Pat. No. 8,002,744.

(60) Provisional application No. 60/954,252, filed on Aug. 6, 2007.

(51) Int. Cl.
*B65H 81/00* (2006.01)

(52) U.S. Cl.
USPC ........... 156/171; 156/173; 156/184; 156/189; 156/190

(58) Field of Classification Search
USPC ......... 156/166, 169, 171, 173, 184, 189, 190, 156/195
See application file for complete search history.

(56) References Cited

U.S. PATENT DOCUMENTS

| | | | |
|---|---|---|---|
| 8,236,221 B2 * | 8/2012 | Pepper et al. | 264/279 |
| 8,313,601 B2 * | 11/2012 | Pepper et al. | 156/189 |
| 2005/0228427 A1 * | 10/2005 | Sridharan et al. | 606/192 |
| 2005/0271844 A1 * | 12/2005 | Mapes et al. | 428/36.1 |
| 2006/0085024 A1 * | 4/2006 | Pepper et al. | 606/192 |

* cited by examiner

*Primary Examiner* — Katarzyna Wyrozebski Lee
*Assistant Examiner* — Carson Gross
(74) *Attorney, Agent, or Firm* — King & Schickli, PLLC

(57) ABSTRACT

A non-compliant fiber-reinforced medical balloon comprises a first fiber layer and a second fiber layer embedded in a continuous matrix of thermally-weldable polymer material defining a barrel wall, cone walls and neck walls. The fibers of the first fiber layer have a pattern of different lengths and are divisible into a first group and a second group based on length. The length of the fibers of the second group varies progressively in accordance to their proximity to the fibers of the first group; the fibers of the second group closest to the fibers of the first group being longer than the fibers of the second group further from the fibers of the first group. The fiber of the second fiber layer winds circumferentially around the longitudinal axis of the balloon substantially over the entire length of the balloon.

15 Claims, 24 Drawing Sheets

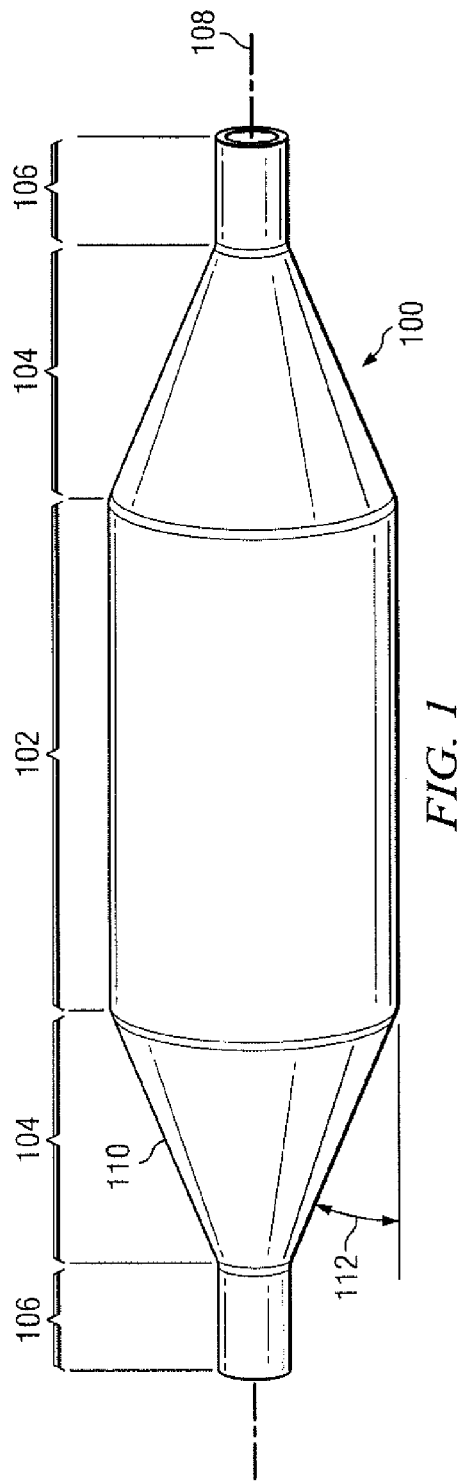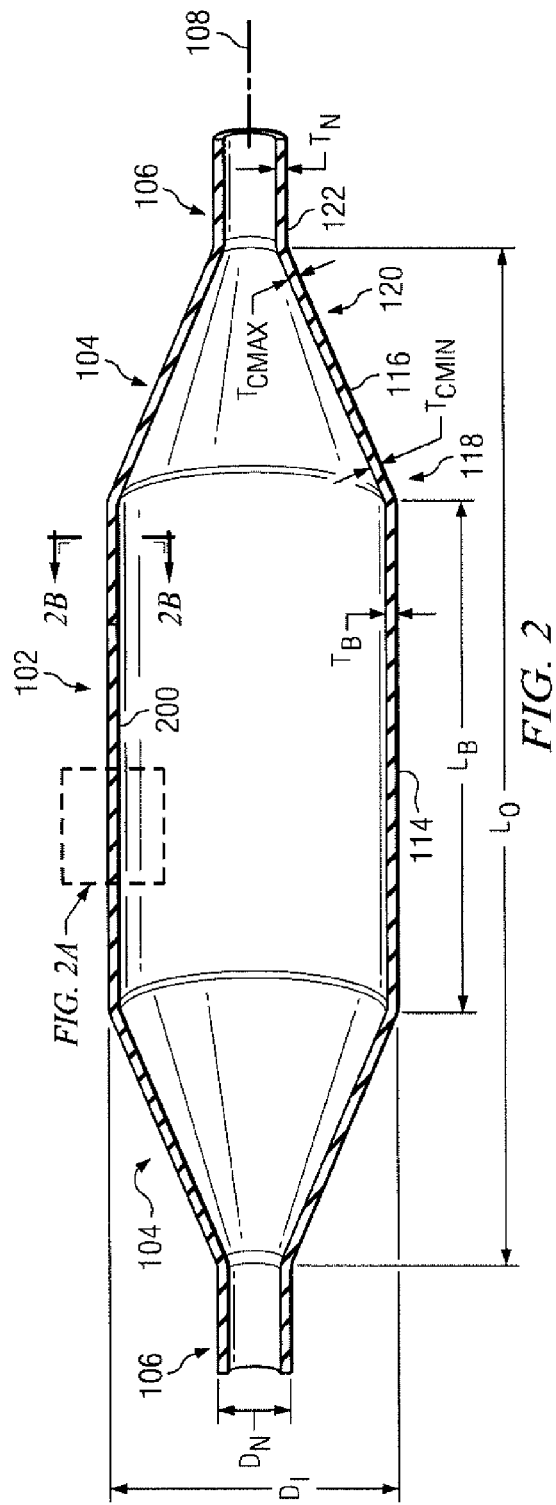

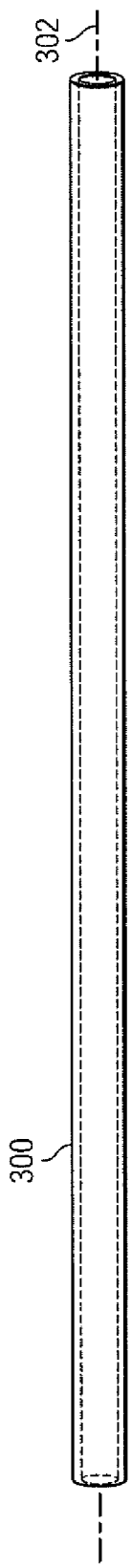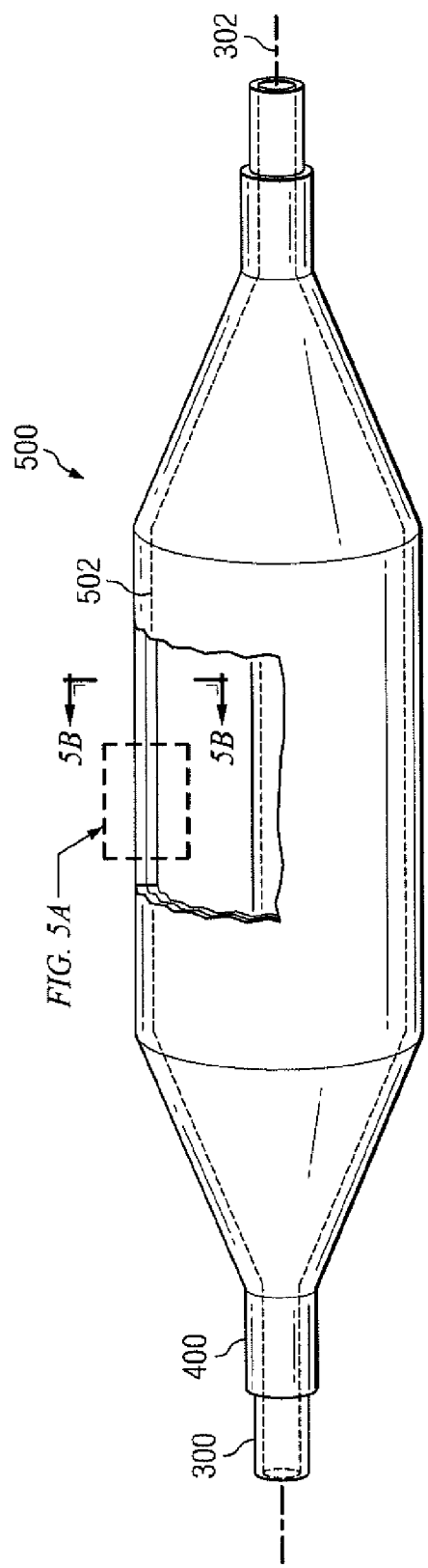

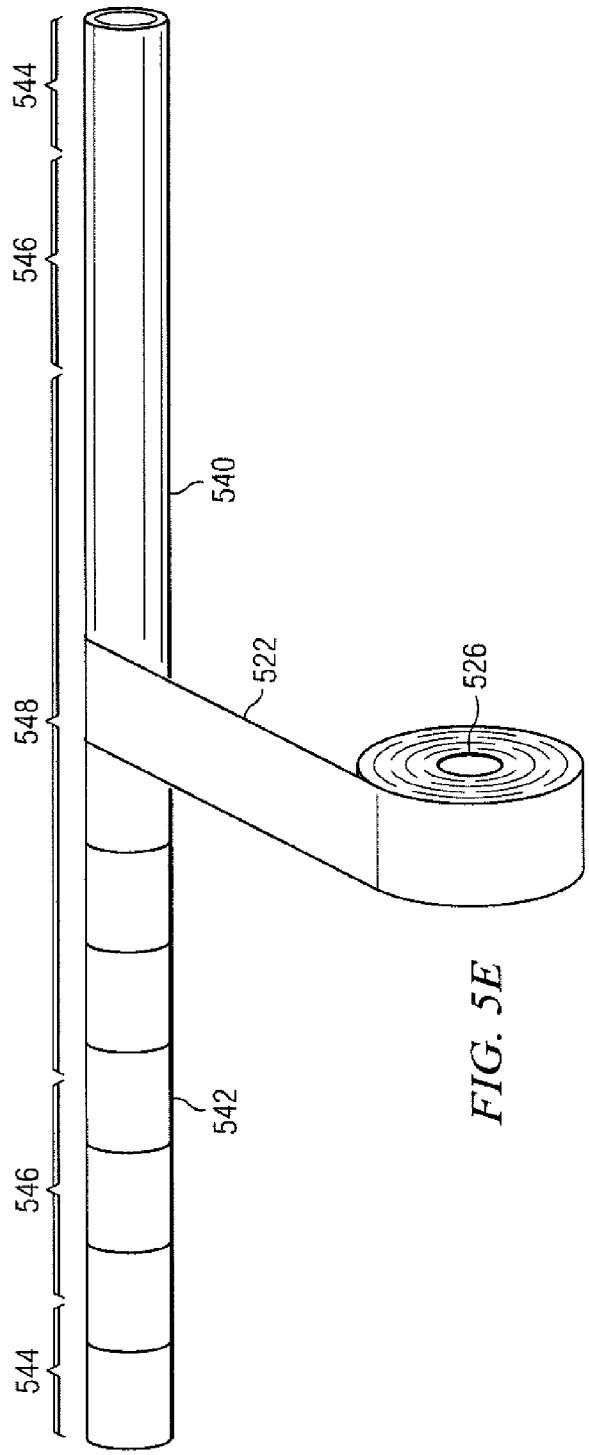
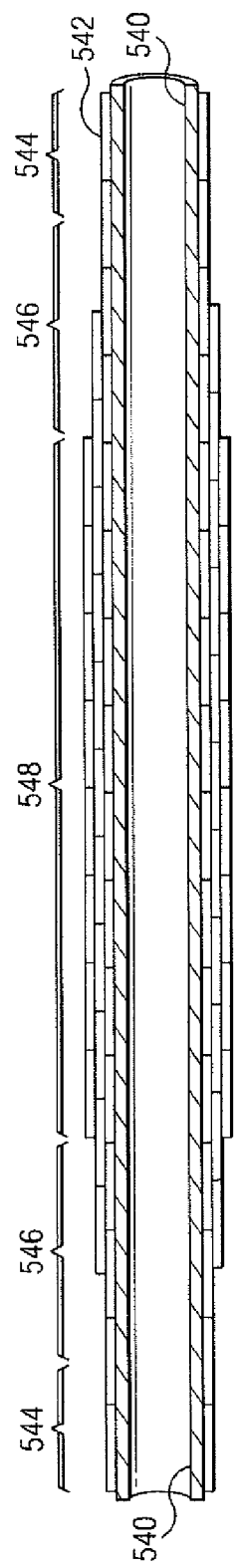
FIG. 5E
FIG. 5F

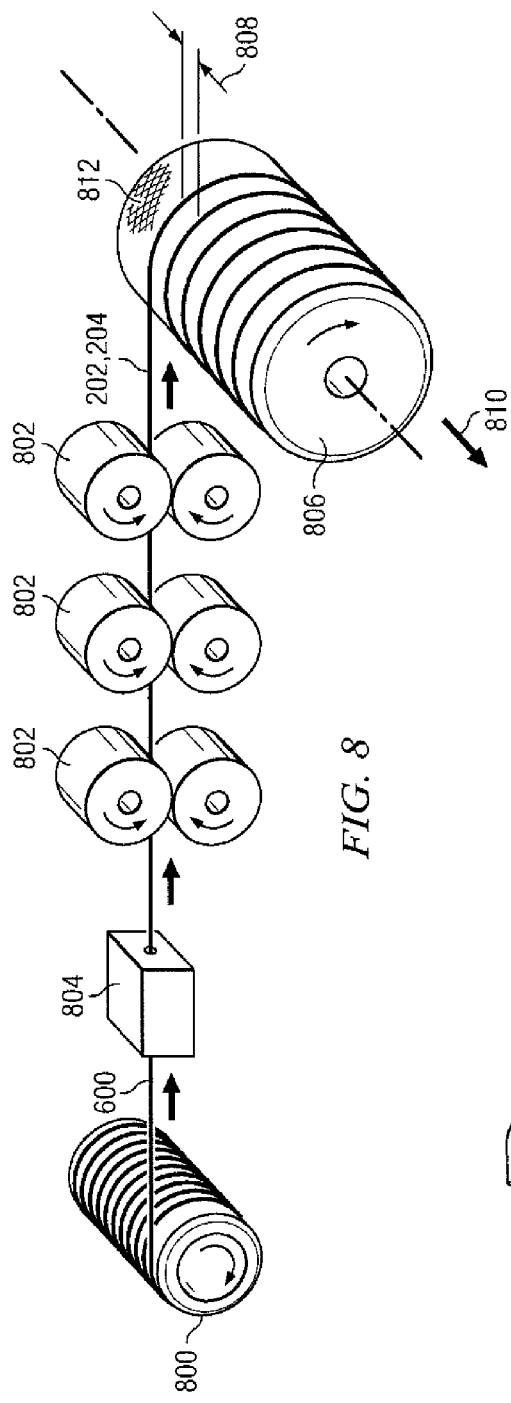
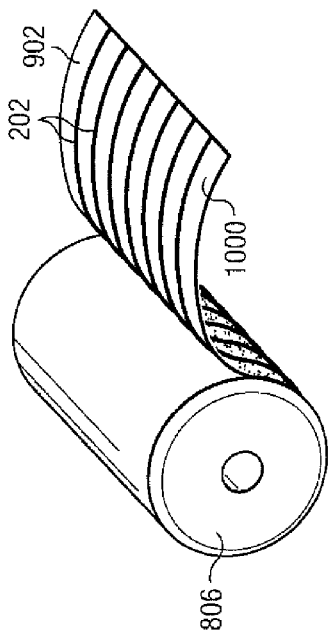
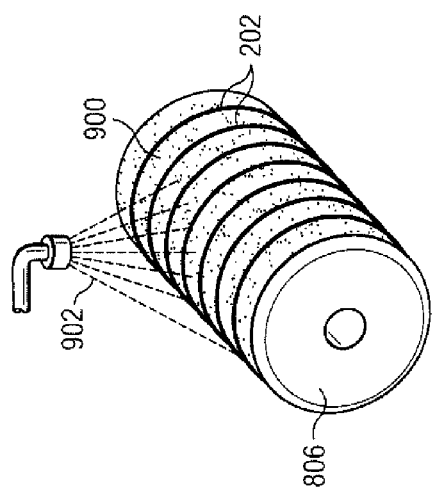
FIG. 8
FIG. 10
FIG. 9

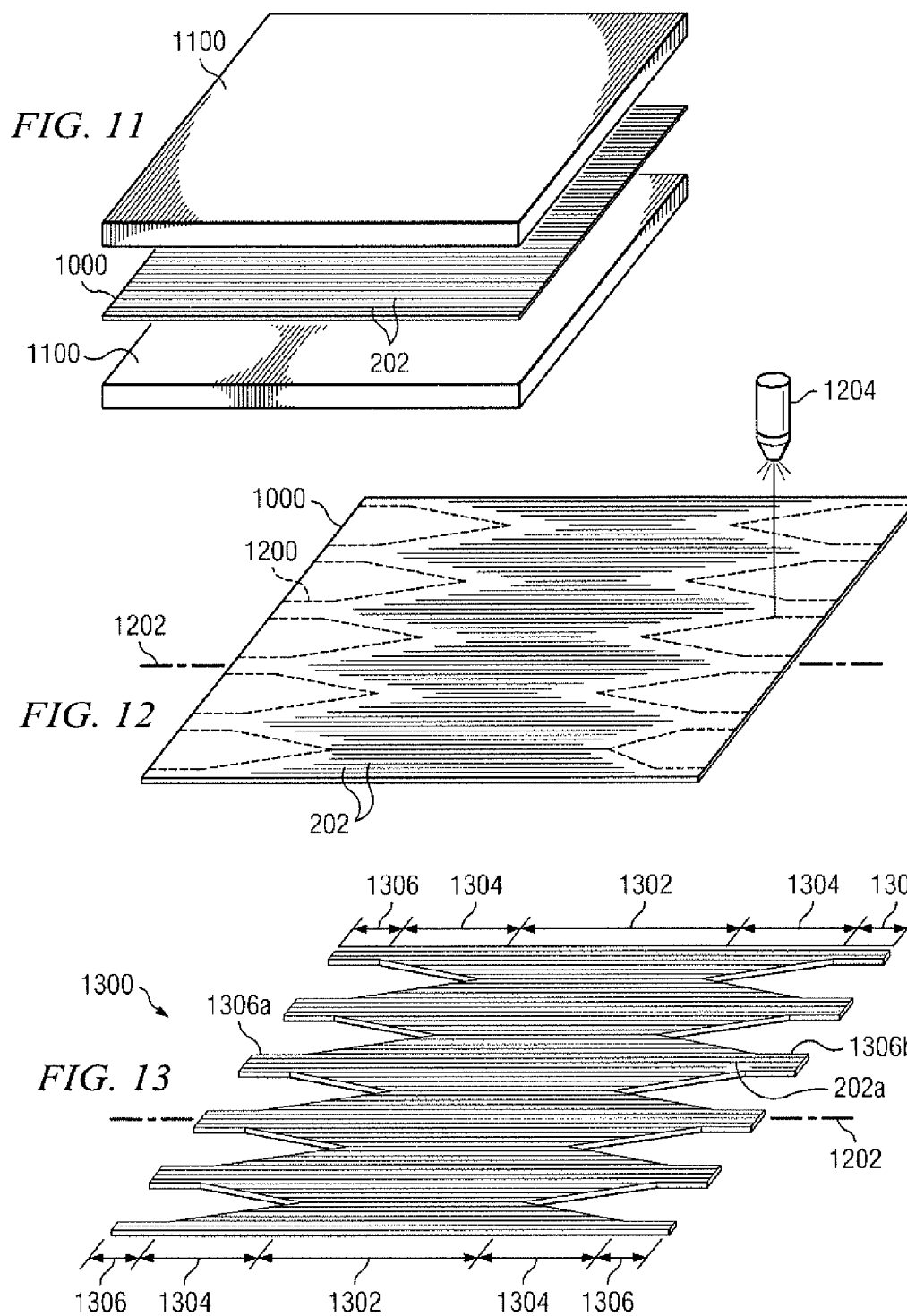

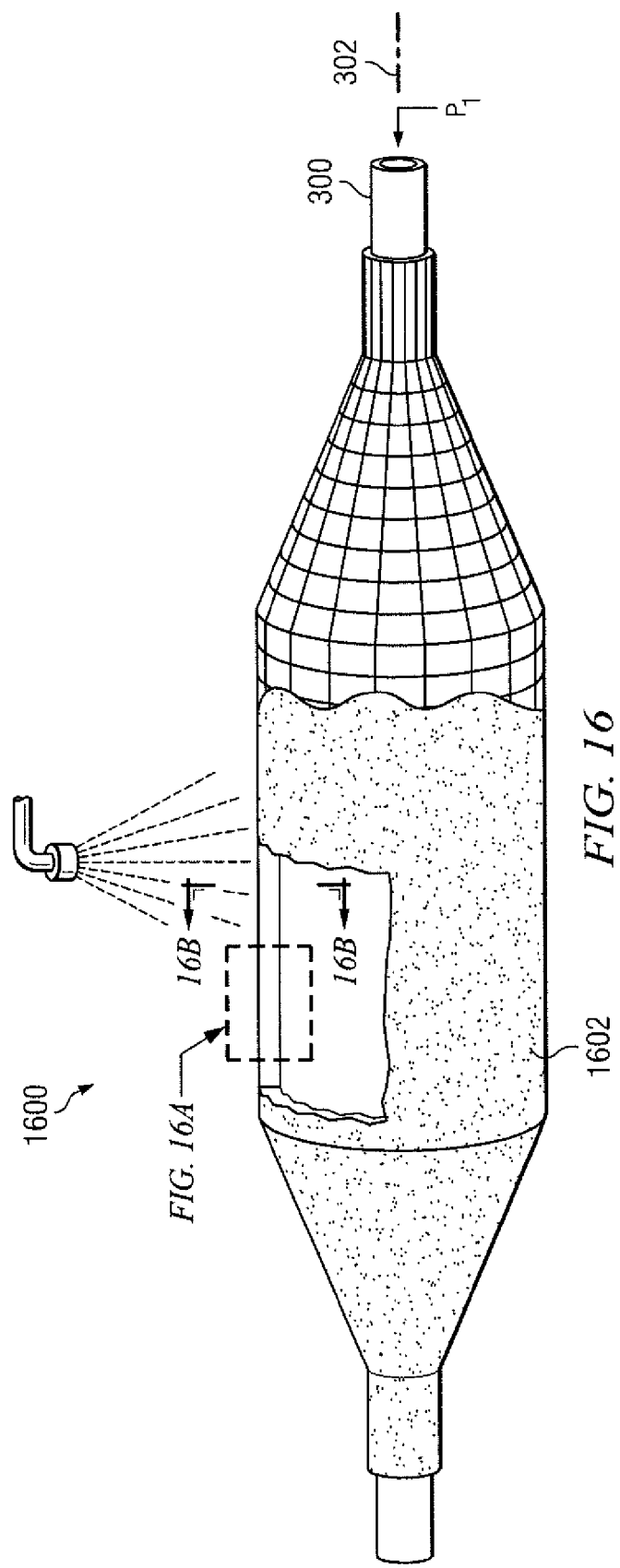

NON-COMPLIANT MEDICAL BALLOON

CROSS-REFERENCE TO RELATED APPLICATIONS

This application is a Continuation-In-Part of pending U.S. application Ser. No. 12/187,259, filed on Aug. 6, 2008 and entitled, "NON-COMPLIANT MEDICAL BALLOON," which claims priority to U.S. Provisional Application Ser. No. 60/954,252, filed on Aug. 6, 2007, and entitled "NON-COMPLIANT MEDICAL BALLOON," the specifications of which are incorporated herein by reference.

TECHNICAL FIELD

This disclosure relates to the field of medical balloons. In particular, it relates to non-compliant medical balloons that are useful in angioplasty and other medical applications including cardiology, radiology, urology and orthopedics.

BACKGROUND

Non-compliant medical balloons for performing angioplasty and other medical procedures are known. U.S. Pat. No. 6,746,425 to Beckham discloses a non-compliant medical balloon and methods for manufacturing the balloon. U.S. Patent Application Publication No. US 2006/0085022 to Hayes et al. discloses a non-compliant medical balloon having an integral woven fabric layer and methods for manufacturing the balloon. U.S. Patent Application Publication No. US 2006/0085023 to Davies, Jr. et al. discloses a medical balloon having strengthening rods and methods for manufacturing the balloon. U.S. Patent Application Publication No. US 2006/0085024 to Pepper et al. discloses a non-compliant medical balloon having an integral non-woven fabric layer and methods for manufacturing the balloon. U.S. Pat. No. 6,746,425 and Publication Nos. US 2006/0085022, US 2006/0085023 and US 2006/0085024 are hereby incorporated herein by reference.

It is desirable to make the outer wall of a non-compliant medical balloon as thin as possible while still maintaining the required pressure rating or burst strength. In non-compliant balloons, the walls typically forms pleats when deflated (i.e., before or after inflation), and these pleats are folded over, wrapped and/or rolled around the long axis of the balloon. The thinner the wall material, the smaller the diameter of the deflated balloon. This smaller diameter facilitates passage of the deflated balloon through narrow vessels, lumens or cavities of the body prior to deployment. The walls of conventional non-compliant balloons include numerous discrete layers and/or components that tend to increase the thickness. A need therefore exists for a medical balloon having thinner walls and/or walls with fewer layers or components.

It is also desirable to make the outer wall of a non-compliant medical balloon as flexible as possible while still maintaining the required pressure rating or burst strength. The flexibility of the deflated balloon directly affects its "trackability," i.e., its ability to traverse sharp turns or branches of the vessels or body cavities through which the balloon must pass. The more flexible the walls, the better the trackability. The walls of conventional balloons often include physical adhesive layers needed to hold the disparate layers together or to prevent the movement of the wall components relative to one another. Unfortunately, some adhesives are frequently stiffer than the materials/components being joined. Thus, these adhesive layers may undesirably increase the stiffness of the balloon walls. A need therefore exists for a medical balloon that eliminates or reduces the presence of adhesives in the finished balloon.

Conventional non-compliant balloons may have a wall thickness that varies considerably at different points of the balloon. For example, the wall thickness of the neck portion may be significantly thicker than the wall thickness of the barrel portion. Further, the wall thickness of the cone portion may vary from a relatively large thickness proximate the neck portion to a relatively low thickness proximate the barrel portion. This variation in wall thickness is frequently caused by the incorporation of blow-molded components (which have inherent wall thickness variability) into the structure of the balloon, but may be caused by other factors as well. Regardless of the cause, thicker walls in portions of the balloon that must be folded tend to affect adversely the user's ability to fold the deflated balloon into the desired diameter. This effect may be especially significant in the cone portion, where thicker cone walls can result in "bulges" at the front and the back of the folded balloon that are larger than the intervening barrel portion and, thus, force the user the increase the size of the introducer used to insert the balloon into the patient. It is thus desirable to develop non-compliant balloon construction methods yielding better control over the wall thickness of the balloon at all portions of the envelope. It is further desirable to make non-complaint medical balloons having relatively uniform wall thickness for the entire envelope, including the barrel, cone and neck portions.

It is still further desirable to simplify the construction of non-compliant medical balloons so as to reduce the amount of time and labor required for manufacture, to reduce the product defect rate, and/or to reduce the cost of production. The conventional construction of non-compliant balloons may require many discrete steps, some or all of which may require precision hand assembly that can be difficult or expensive to automate. A need therefore exists for improved methods of manufacturing non-compliant medical balloons.

SUMMARY

In one aspect thereof, there is disclosed a non-compliant fiber-reinforced medical balloon that may be inflated and deflated, and when inflated exhibits minimal change in radial distension across a predetermined range of internal pressures. The balloon has a generally cylindrical barrel wall disposed between tapered cone walls and cylindrical neck walls extending therefrom along a longitudinal axis. The balloon comprises a first fiber layer and a second fiber layer embedded in a continuous matrix of thermally-weldable polymer material defining a barrel wall, cone walls and neck walls. The fibers of the first fiber layer run substantially parallel to one another and substantially parallel to the longitudinal axis of the balloon. The fibers of the first fiber layer have a pattern of different lengths and are divisible into a first group and a second group based on length. Each fiber of the first group begins in the neck wall at one end of the balloon, extends continuously in the longitudinal direction and terminates in the neck wall at the opposite end of the balloon. Substantially all of the fibers of the first group have a generally uniform length. Each fiber of the second group begins in the cone wall at one end of the balloon, extends continuously in the longitudinal direction and terminates in the cone wall at the opposite end of the balloon. The length of the fibers of the second group varies progressively in accordance to their proximity to the fibers of the first group. The fibers of the second group closest to the fibers of the first group are longer than the fibers of the second group further from the fibers of the first group.

The fiber of the second fiber layer winds circumferentially around the longitudinal axis of the balloon substantially over the entire length of the balloon including the neck walls, the cone walls and the barrel wall.

In another aspect thereof, there is disclosed a non-compliant medical balloon that may be inflated and deflated, and when inflated exhibits minimal change in radial distension across a predetermined range of internal pressures. The balloon has a generally cylindrical barrel wall disposed between tapered cone walls and cylindrical neck walls extending therefrom along a longitudinal axis. The balloon comprises an inner layer of thermally-weldable polymer material, a first fiber/polymer matrix layer disposed over the inner layer, a second fiber/polymer matrix layer disposed over the first fiber/polymer matrix layer, and an outer layer of thermally-weldable polymer material disposed over the second fiber/polymer matrix layer. The fibers of the first fiber/polymer matrix layer are substantially inelastic and run substantially parallel to one another and substantially parallel to the longitudinal axis of the balloon. The polymer of the first fiber/polymer matrix layer is a thermally-weldable polymer material. The fibers of the second fiber/polymer matrix layer are substantially inelastic and wind circumferentially around the longitudinal axis of the balloon substantially over the entire length of the balloon. The polymer of the second fiber/polymer matrix layer is a thermally-weldable polymer material. All of the thermally-weldable polymer materials from each of the layers have been fused together into a continuous polymer matrix encapsulating the fibers of the first and second fiber/polymer matrix layers and defining a barrel wall, cone walls and neck walls.

In another aspect, a method of making non-compliant fiber-reinforced medical balloon is disclosed. The method includes the steps of: (1) embedding a first fiber layer in a continuous matrix of thermally-weldable polymer, (2) cutting the first fiber layer in a pattern defining the generally cylindrical barrel wall, tapered cone walls and cylindrical neck walls wherein the fibers of the first fiber layer extend substantially parallel to the longitudinal axis of the balloon, and (3) wrapping the fiber of the second fiber layer circumferentially around the longitudinal axis of the balloon substantially over the entire length of the balloon including the neck walls, the cone walls and the barrel wall. In one embodiment, the fibers of the first fiber layer have a pattern of different lengths and are divisible into a first group and a second group based on length. The fibers of the first group begin in the neck wall at one end of the balloon, and extend continuously in the longitudinal direction and terminate in the neck wall at the opposite end of the balloon. The fiber of the second group begins in the cone wall at one end of the balloon and extends continuously in the longitudinal direction and terminating in the cone wall at the opposite end of the balloon. The length of the fibers of the second group vary progressively in accordance to their proximity to the fibers of the first group with the fibers of the second group closest to the fibers of the first group being longer than the fibers of the second group further from the fibers of the first group. In one variation, the first fiber layer is affixed over a mandrel before wrapping the fiber of the second fiber layer around the balloon. The method may further include embedding the second fiber layer in the continuous matrix of thermally-weldable polymer.

In yet another aspect, a non-compliant fiber-reinforced medical balloon that may be inflated and deflated, and when inflated exhibits minimal change in radial distension across a predetermined range of internal pressures includes a generally cylindrical barrel wall disposed between tapered cone walls and cylindrical neck walls extending therefrom along a longitudinal axis. The balloon includes a first textile layer comprising a plurality of substantially inelastic fibers embedded in a continuous matrix of thermally-weldable polymer material defining a barrel wall, cone walls and neck walls. The first textile layer may be one of a woven, knitted, braided or non-woven textile material. The balloon further includes a fiber layer wherein the fiber winds circumferentially around the longitudinal axis of the balloon substantially over the entire length of the balloon including the neck walls, the cone walls and the barrel wall. In one variation, the balloon includes an outer layer of thermally-weldable polymer material disposed over the second textile layer. The thermally-weldable polymer materials from each of the layers may be fused together into a continuous polymer matrix encapsulating the fibers of the first and second fiber/polymer matrix layers and defining the barrel wall, cone walls and neck walls.

In yet another aspect, a method of making non-compliant fiber-reinforced medical balloon that may be inflated and deflated, and when inflated exhibits minimal change in radial distension across a predetermined range of internal pressures, the balloon having a generally cylindrical barrel wall disposed between tapered cone walls and cylindrical neck walls extending therefrom along a longitudinal axis, includes forming a forming a first fiber layer in a pattern The pattern includes a plurality of generally rectangular barrel regions with tapered cone regions on each end of each of the tapered barrel regions. Generally rectangular neck regions extend from each of the tapered cone regions such that the tapered cone regions connect the neck regions and barrel regions. The barrel regions of the pattern are each connected continuously along the length of a side thereof to an adjacent barrel region whereby the first fiber layer defines the generally cylindrical barrel wall, tapered cone walls and cylindrical neck walls when wrapped around a mandrel.

An inner thermally weldable polymer layer is formed by one of spraying, brushing or dipping a solution including a thermally weldable polymer material onto a preformed mandrel. Alternatively the inner may be formed by wrapping a tubular or preformed mandrel with a tape or film formed from a thermally welded polymer material and/or b) placing a tube of a thermally welded polymer material over a tubular or preformed mandrel. The patterned first fiber layer is placed over the inner layer, and a second fiber layer is formed with circumferential wraps over the first fiber layer. In one embodiment, a solution including a thermally weldable polymer over the first fiber layer by spraying, dipping or brushing before forming the second fiber layer after which the solution may be applied over the second fiber layer. In one embodiment, a film or tape formed from a thermally weldable polymer material is wrapped over the over the first and second fiber layers. The mandrel with the applied layers of material may then be heated to embed the first and second fiber layers in a continuous matrix of thermally weldable polymer material.

BRIEF DESCRIPTION OF THE DRAWINGS

For a more complete understanding, reference is now made to the following description taken in conjunction with the accompanying Drawings in which:

FIG. 1 is a side view of a medical balloon in accordance with one embodiment;

FIG. 2 is a cross-sectional side view of the medical balloon of FIG. 1;

FIG. 3 a side view of a raw mandrel tube prior to blow-molding;

FIG. 4 shows the mandrel tube of FIG. 3 fitted with a polymer sleeve prior to blow-molding;

FIG. 5 shows the removable mandrel with conformal layer after blow-molding;

FIG. 5E illustrates one method of forming a base layer or sleeve on a formable mandrel by means of winding a tape of thermally weldable material around the mandrel;

FIG. 5F is a partial cross-sectional view of the base layer and mandrel of FIG. 5E after the winding operation is completed;

FIG. 8 illustrates forming flattened reinforcing fibers and preparing fiber-reinforced polymer sheets in accordance with additional embodiments;

FIG. 9 illustrates coating the reinforcing fibers with polymer material during preparation of fiber-reinforced polymer sheets in accordance with additional embodiments;

FIG. 10 illustrates removing sheets of polymer embedded with reinforcing fibers during preparation of fiber-reinforced polymer sheets in accordance with additional embodiments;

FIG. 11 illustrates fusing and flattening fiber-reinforced polymer sheets in accordance with additional embodiments;

FIG. 12 illustrates patterning and cutting a pre-fabricated fiber-reinforced balloon wall layer (also called a "sock") in accordance with additional embodiments;

FIG. 13 shows a perspective view of a patterned sock, i.e., a prefabricated fiber-reinforced balloon wall layer, in accordance with additional embodiments;

FIG. 16 illustrates applying a third coating layer over the in-progress balloon and mandrel in accordance with additional embodiments;

DETAILED DESCRIPTION

Figure 2A:
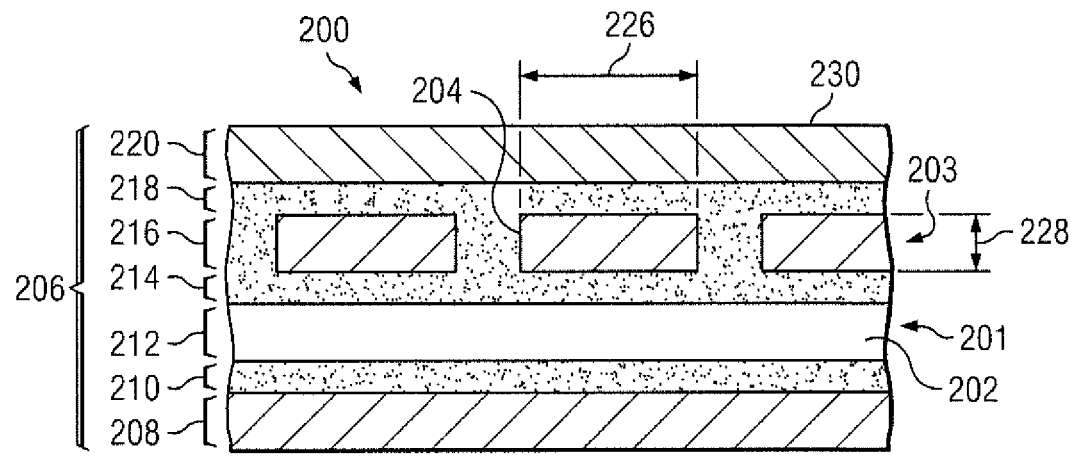
FIG. 2A is an enlarged cross-sectional view of the balloon wall looking in the circumferential direction taken along line 2A-2A of FIG. 2.

Referring now to the drawings, wherein like reference numbers are used herein to designate like elements throughout, the various views and embodiments of a non-compliant medical balloon are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Referring now to FIG. 1, there is illustrated a non-complaint medical balloon in accordance with one aspect, shown in its fully inflated state. Balloon 100 includes a generally cylindrical barrel portion 102 disposed between tapered cone portions 104 and cylindrical neck portions 106 extending therefrom along a longitudinal axis 108. The outer surface 110 of the cone portion 104 forms an angle 112 (the "cone angle") with respect to a longitudinal extension of the wall of the barrel portion 102. Conventional non-compliant balloons are typically limited to cone angles in the range of about 12 degrees to 16 degrees in order to minimize bulging (when folded) due to the thickness of the cone walls. As described further herein, embodiments of the balloon 100 may have a cone angle 112 in the range of 12 degrees to 22 degrees. In preferred embodiments, the cone angle 112 is in the range of 18 degrees to 22 degrees, and in more preferred embodiments, the cone angle 112 is about 20 degrees. The higher cone angle 112 results in shorter overall length for the balloon for a given barrel length.

Referring now to FIG. 2, a balloon 100 is shown in cross-section to illustrate further its structure. The diameter of the barrel portion 102 of the balloon ranges between a maximum size when inflated, denoted $D_I$, and a minimum size when deflated and folded, denoted $D_D$ (not shown). The diameter of the neck portion 106, denoted $D_N$, stays substantially constant regardless of inflation state. In preferred embodiments, the deflated diameter $D_D$ of the balloon is substantially equal to the neck diameter $D_N$. The barrel portion 102 of the balloon has a length, denoted $L_B$, measured between cone portions 104. The overall length, denoted $L_O$, is generally measured to the outer ends of the cone portions 104.

The walls of the balloon 100 include a barrel wall 114 having a relatively constant thickness, denoted $T_B$, cone walls 116 having a thickness ranging from a minimum, denoted $T_{CMIN}$, to a maximum, denoted $T_{CMAX}$, and neck walls 122 having a relatively constant thickness, denoted $T_N$. In prior art non-compliant balloons, $T_{CMIN}$ was often located near the barrel end 118 of the cone wall 116 and $T_{CMAX}$ was often located near the neck-end 120. In the improved balloons disclosed herein, $T_{CMIN}$ and $T_{CMAX}$ may be disposed at locations other than those shown, and in some embodiments the wall thickness along the cone wall 116 may be essentially constant such that $T_{CMIN}$ and $T_{CMAX}$ are approximately equal. In preferred embodiments, the cone walls 116 of balloon 100 have a relatively constant thickness such that the difference between $T_{CMAX}$ and $T_{CMIN}$ is not greater than ±10% of $T_{CMIN}$. More preferably, the difference between $T_{CMAX}$ and $T_{CMIN}$ is not greater than ±5% of $T_{CMIN}$. In still further embodiments, the thickness of the barrel wall 114 and cone walls 116 (collectively referred to as the "folding walls" since they must be folded when the balloon is in the deflated state to achieve the minimum diameter $D_D$) are substantially equal such that the difference between wall thicknesses $T_B$, $T_{CMIN}$ and $T_{CMAX}$ is not greater than ±10% of $T_B$. More preferably, the maximum difference between the folding wall thicknesses $T_B$, $T_{CMIN}$ and $T_{CMAX}$ is not greater than ±5% of $T_B$.

Figure 2B:
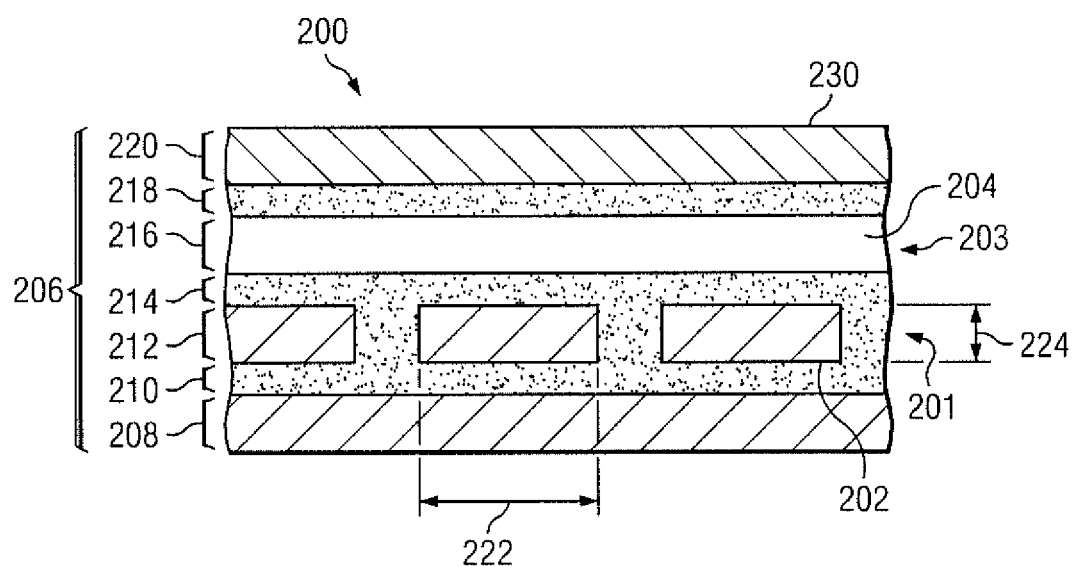
FIG. 2B is an enlarged cross-sectional view of the balloon wall looking in the longitudinal direction taken along line 2B-2B of FIG. 2.

Referring now to FIGS. 2A and 2B, enlarged cross-sections of the wall of balloon 100 are shown to illustrate the structure further. Although the illustrated cross-sections are taken through the barrel wall 114, as further disclosed herein the wall structures in the barrel wall 114, cone walls 116 and neck walls 122 are substantially identical to one another and will therefore collectively be identified as balloon wall 200. The balloon wall 200 has a composite structure including a first layer 201 of longitudinally-oriented reinforcing fibers 202 and second layer 203 of circumferentially- or "hoop-" oriented reinforcing fibers 204 embedded in a matrix 206 of thermally-weldable polymer material. The matrix 206 may be a single material or it may comprise multiple regions of compatible thermally-weldable polymer material that have been thermally welded into a continuous matrix. It will be appreciated that thermal welding, wherein heat and pressure alone are used to form a bond between the materials being joined, is differentiated from adhesive bonding, wherein an adhesive material is introduced between the materials being joined. In the illustrated embodiment, the matrix material 206 comprises an inner region 208, a first coating region 210, a sock region 212 (disposed primarily between the longitudinal fibers 202), a second coating region 214, a third coating region 216, a fourth coating region 218 and an outer region 220, all of which are compatible thermally-weldable materials. Preferably, the matrix 206 does not include any adhesive layers.

In one embodiment, the matrix 206 may be formed of thermally-weldable nylon (i.e., aliphatic polyamide) or polyamide blend. In another embodiment, the first coating region 210, the sock region 212, the second coating region 214, the third coating region 216 and the fourth coating region 218 are formed of soluble nylon and the inner region 208 and the outer region 220 are formed of a polyether block amide (PEBA), a nylon-containing thermoplastic blend, having a durometer hardness in the range from about Shore D 25 to about Shore D 54. Since both materials contain substantial parts nylon, they are thermal-welding compatible. In a preferred embodiment, the first coating region 210, the sock region 212, the second coating region 214, the third coating region 216 and the fourth coating region 218 are formed of soluble nylon and the inner region 208 and the outer region 220 are formed of Type-5533 PEBAX® brand PEBA having a durometer hardness of about Shore D 55.

It will be appreciated that the thickness of the fibers and regions in FIGS. 2A and 2B are not necessarily shown to scale. Also, some of the matrix regions may not be present in every portion of the balloon wall 200. For example, in some embodiments the second coating region 214 may be disposed only in the cone walls 116 portion of the balloon wall.

The longitudinally-oriented reinforcing fibers 202 are substantially inelastic fibers oriented parallel or substantially parallel to one another and parallel within ±10 degrees to the balloon's longitudinal axis 108. The circumferentially- or hoop-oriented reinforcing fibers 204 are substantially inelastic fibers oriented parallel or substantially parallel to one another and perpendicular within ±10 degrees to the longitudinally-oriented reinforcing fibers 202. The reinforcing fibers 202 and 204 may be formed of a variety of inelastic materials, including, but not limited to, Kevlar, Vectran, Spectra, Dacron, Dyneema, Turlon (PBT), Zylon (PBO), polyimide (PIM) and other ultrahigh molecular weight polyethylenes, aramids, and the like. In one embodiment, the longitudinal fibers 202 and the hoop fibers 204 may be aramid fibers, preferably multi-filament. In another embodiment, the longitudinal fibers 202 and the hoop fibers 204 may be para-aramid fibers, multi-filament. In a preferred embodiment, the longitudinal fibers 202 and the hoop fibers 204 may be Technora® brand paraphenylene/3,4-oxydiphenylene/terephthalamide copolymer, preferably multi-filament. The material of the reinforcing fibers 202 and 204 need not be thermally-weldable since the fibers are encapsulated in the matrix 206, however, the fiber material must be thermally compatible with the matrix material. In this context, the term "thermally compatible" is used to indicate that the material of the reinforcing fibers 202 and 204 can withstand the heat and temperatures, required for thermal welding of the materials forming the matrix 206 without material degradation.

Referring still to FIGS. 2A and 2B, the longitudinal reinforcing fibers 202 have a width 222 and a thickness 224, and the hoop reinforcing fibers 204 have a width 226 and a thickness 228. Preferably, the reinforcing fibers 202 and 204 are "flattened" to reduce the overall thickness of the balloon wall 200 while maintaining the same cross-sectional area. In some embodiments, the longitudinal fibers 202 have a width-to-thickness ratio in the range from about 25:1 to about 45:1, and in preferred embodiments, the longitudinal fibers 202 have a width-to-thickness ratio in the range from about 30:1 to about 40:1. In some embodiments, the hoop fibers 204 have a width-to-thickness ratio in the range from about 25:1 to about 45:1, and in preferred embodiments, the hoop fibers 204 have a width-to-thickness ratio in the range from about 30:1 to about 40:1.

Although the balloon 100 may be constructed to any dimensions, balloons having a deflated diameter $D_D$ in the range from about 4 French Units (i.e., about 0.053 inches or 1.35 millimeters) to about 12 French Units (i.e., about 0.158 inches or 4.0 millimeters) are particularly useful in the fields of cardiology, radiology, orthopedics and urology. Producing such small diameter non-complaint balloons requires extremely thin balloon walls. In one embodiment, balloon 100 is a medical balloon having a deflated diameter $D_D$ in the range of 4 to 12 French Units and a folding wall thickness (i.e., $T_B$ and $T_{CMAX}$) in the range of about 0.001 inches to about 0.0023 inches (per wall). In another embodiment, balloon 100 is a medical balloon having a deflated diameter $D_D$ in the range of 4 to 12 French Units and a folding wall thickness in the range of about 0.0015 inches to about 0.0020 inches (per wall). In yet another embodiment, balloon 100 is a medical balloon having a deflated diameter $D_D$ in the range of 4 to 6 French Units and a folding wall thickness in the range of about 0.001 inches to about 0.0020 inches (per wall).

Referring now to FIGS. 3-22, details of the medical balloon 100 and methods for manufacturing such balloons are disclosed. In some embodiments, all of the longitudinal reinforcing fibers 202 may be attached to the balloon structure as part of a pre-formed sheet called a "sock." Use of this sock process may significantly simplify assembly of the balloon 100, reduce costs, improved quality and/or yield other benefits.

Referring first to FIG. 3, one method of construction of the balloon 100 begins with formation of a removable semi-compliant mandrel. The mandrel begins as a raw mandrel tube 300 comprising a tube of blow moldable material, such as polyethylene terephthalate (PET). The tube 300 has a longitudinal axis 302. For balloons in the 4 to 12 French Unit size, the raw mandrel tube 300 will typically have an outer diameter (O.D.) of about 0.05 inches to about 0.15 inches and a wall thickness of about 0.010 inches to about 0.020 inches.

Referring now to FIG. 4, an inner sleeve 400 of balloon matrix material is placed over the raw mandrel tube 300 prior to blow molding. The inner sleeve 400 will not become part of the removable mandrel; rather, it will become an integral part of the finished balloon, namely, the inner region 208 of the matrix 206. Accordingly, the materials of the raw mandrel tube 300 and of the inner sleeve 400 must be selected such that they do not thermally weld or otherwise stick together during subsequent operations as the balloon is constructed. For a mandrel formed of PET, the inner sleeve 400 may be formed of PEBA, such as Pebax®. For balloons in the 4 to 12 French Unit size, inner sleeve 400 may be formed of PEBA having a thickness of about 0.004 inches to about 0.005 inches per wall (before blow molding).

Figure 5A:
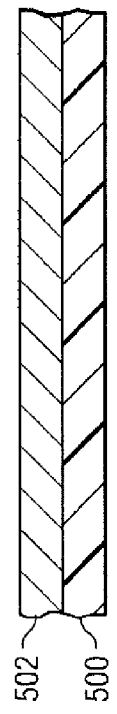
FIG. 5A is an enlarged cross-sectional view of the in-progress balloon wall overlying the mandrel looking in the circumferential direction taken along line 5A-5A of FIG. 5.
Figure 5B:
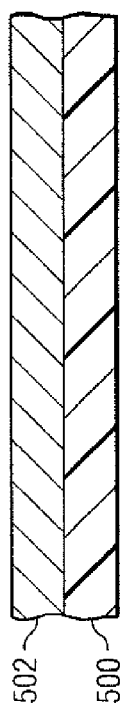
FIG. 5B is an enlarged cross-sectional view of the in-progress balloon wall overlying the mandrel looking in the longitudinal direction taken along line 5B-5B of FIG. 5.

Referring now to FIGS. 5, 5A and 5B, the raw mandrel tube 300 with the inner sleeve 400 in place is blow-molded using conventional techniques to form a balloon-shaped semi-compliant mandrel 500 covered by a conformal layer 502 of material from the sleeve 400. The longitudinal axis 302 of the raw mandrel tube 300 now becomes the longitudinal axis of the mandrel 500. The conformal layer 502 will ultimately become the inner region 208 of the balloon wall 200. As best seen in FIGS. 5A and 5B, the walls of the mandrel 500 and the conformal layer 502 are generally uniform when viewed in cross-section in either the circumferential or longitudinal direction. When constructing balloons 100 in the 4 to 12 French Unit size, the wall thickness of the mandrel 500 after blow-molding may be within the range of about 0.005 inches to about 0.0015 inches along the barrel, and the thickness (per wall) of the conformal layer 502 after blow-molding may be in the range of about 0.0003 inches to about 0.0006 inches. The shape of the mandrel 500 is maintained during the balloon-construction process by internally pressurizing the mandrel to a predetermined pressure.

Figure 5C:
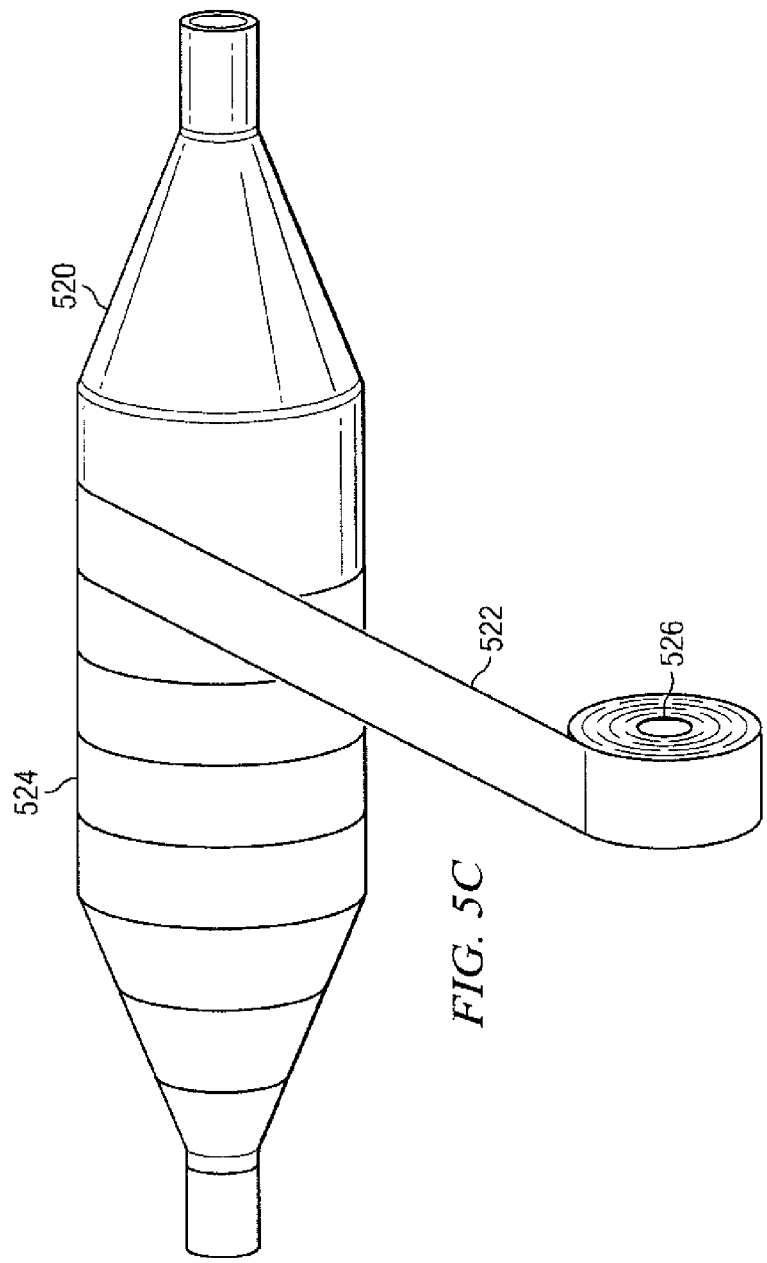
FIG. 5C illustrates one method of forming a base layer or sleeve on a preformed mandrel by means of wrapping the preformed mandrel with a thermally weldable tape.

Referring to FIG. 5C, in one embodiment a method of making balloon 100 (FIG. 1) utilizes a pre-formed removable mandrel 520 to form a base layer or inner layer 524. The preformed mandrel 520 may comprise a moldable material, such as polyethylene terephthalate (PET) that has been blow molded or otherwise formed into the desired configuration using conventional techniques. In other embodiments, mandrel 520 may be a collapsible metal form or the mandrel may be formed from other materials such as a soluble wax or foam material that may be removed from the finished balloon by means of heat or a solvent.

A film or tape 522 formed from a thermally weldable material such as nylon or a polyether block amide such as PEBAX® supplied from a spool 526 of tape is wound around mandrel 520 to form a base layer 524 (corresponding to inner region 208 of FIG. 2). In some embodiments, tape 522 may be wrapped over tube 400 of FIGS. 4 and 5 to form base layer 524. In order to control the thickness of base layer 524, the pitch, or number of wraps of tape 522 per inch may be varied along the length of mandrel 520 to provide the desired overlap, if any, of the wraps.

Controlled circumferential winding of tape 522 may be accomplished by revolving spool 526 around mandrel 520 while indexing the mandrel past the spool. Depending upon the desired thickness of base layer 524 in various regions of the balloon, mandrel 520 may indexed past spool 526 at a variable rate. For example, in the cone regions, mandrel 520 may be indexed past spool 526 at relatively high rate such that there is little or no overlap of successive winds of tape 522. Alternatively in the barrel region, mandrel 520 may be indexed at a slower rate to achieve substantial overlap of the winds and a thicker finished wall thickness. In some embodiments, mandrel 520 may be indexed back and forth relative to spool 526 over selected portions of the mandrel to provide multiple layers of overlapping tape 522 in the selected areas.

In other embodiments, mandrel 520 may be rotated as spool 526 is indexed along the length of the mandrel at a controlled, variable rate. Thus, the pitch at which tape 522 is applied to mandrel 520 may be controlled by varying the linear speed at which mandrel 520 is indexed past spool 526 or vice versa. Alternatively, the pitch or number of wraps of tape 522 may be varied by changing the rate at which tape 522 is wound onto mandrel 520 while indexing the mandrel 500 (or spool 526) at a constant linear speed. After the winding operation is completed, mandrel 520 with tape 522 may be heated in a mold to fuse the wraps of the tape together to form a smooth, continuous base layer 524. In some embodiments, reinforcing fibers and an outer layer of thermally weldable material may be applied over base layer 524 before the molding process.

Figure 5D:
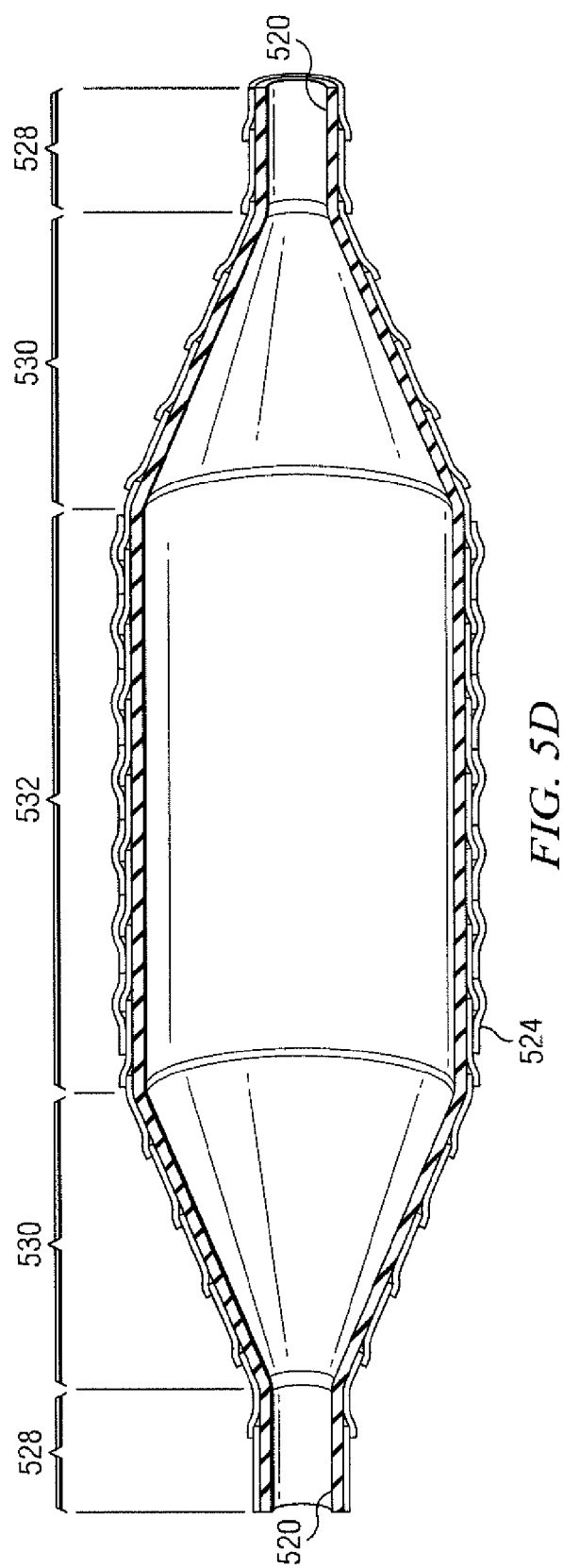
FIG. 5D is a partial cross-sectional view of the base layer and mandrel of FIG. 5C after the winding operation is completed.

FIG. 5D is a longitudinal sectional view of a base layer or inner layer 524 formed on preformed mandrel 520 using tape 522 as described above. As illustrated, the number of wraps of tape 522 in the neck and cone sections of 528, 530 of base layer 524 is less than the number of wraps in the barrel section 532 of the base layer. Reducing the number of wraps in the cone areas 530 reduces the wall thickness of the finished balloon in the cone areas and reduces "bulges" in the finished folded balloon that would otherwise require the use of a larger introducer.

Turning to FIGS. 5E and 5F, in another embodiment, a layer of base material 542 is formed over a formable, tubular mandrel 540 by wrapping or winding tape 522 around the mandrel. Mandrel 540 is formed from a material, such as polyethylene terephthalate (PET) that may be stretch blow molded into the desired configuration using conventional techniques. As best illustrated in FIG. 5F, the number of wraps of tape 522 in the areas 544 and 546 that will ultimately form the neck and cone sections, respectively, of a finished balloon may be less than the number of wraps in area 548 which will become the barrel section of the balloon. Similarly, the number of wraps of tape 522 within each of the areas 544 and 546 may vary in order to achieve the desired wall thickness in the finished balloon. Controlled circumferential winding of tape 522 may be accomplished by revolving spool 526 around mandrel 540 while indexing the mandrel past the spool or alternatively, indexing the spool along the length of the mandrel while rotating the mandrel. After the winding process is completed, mandrel 540 with the desired wraps of tape 522 may be placed in a heated mold and stretch blow molded into the desired final form.

As will be appreciated, during the stretch blow molding process, barrel area 548 will be expanded to a greater degree than neck areas 544 and cone areas 546. However, controlling the number of wraps of tape 522 along the length of mandrel 540 enables control of the wall thickness of the finished base layer 524 along the length of the balloon. In this manner, the wall thickness of the finished balloon in cone areas 546 may be controlled to eliminate or minimize the formation of bulges in the cone areas while maintaining the desired wall thickness in barrel area 548.

Figure 5G:
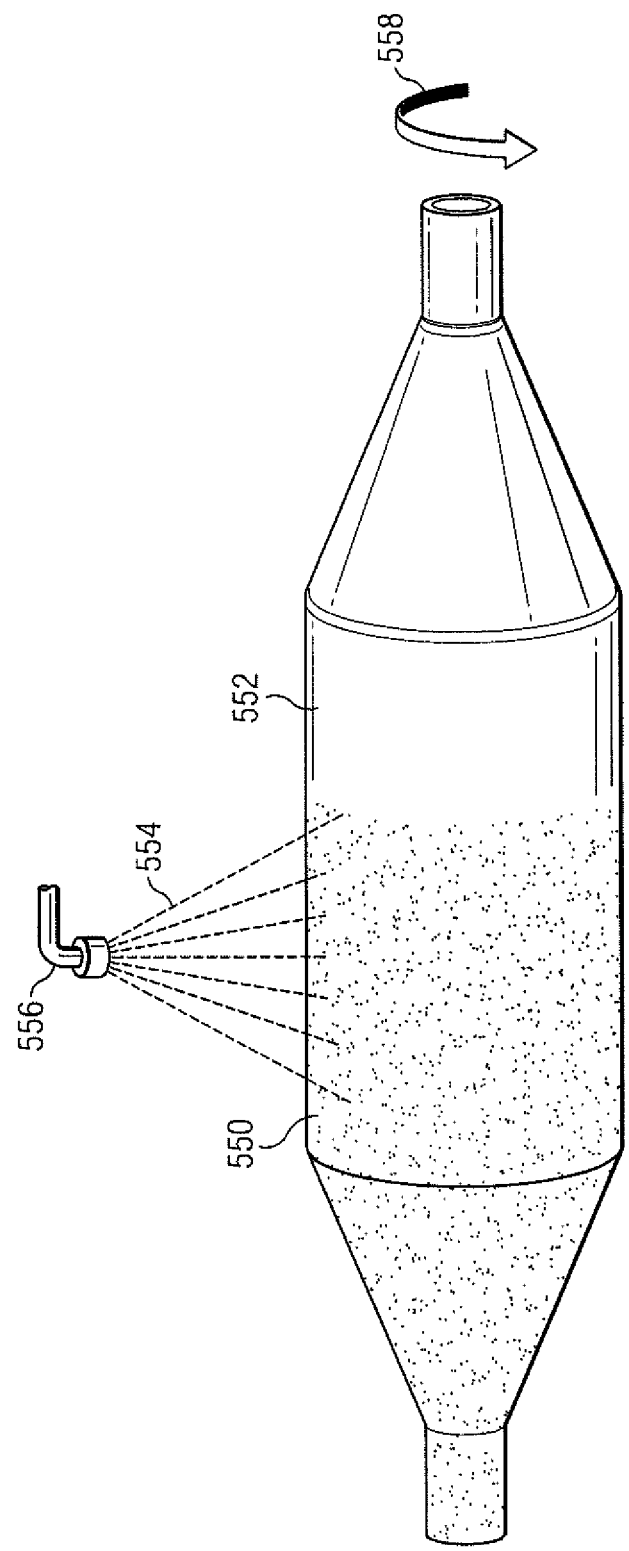
FIG. 5G illustrates a method of forming a base layer or inner layer on a preformed mandrel by means of spraying a solution including a thermally weldable material onto the mandrel.

Turning to FIG. 5G, in yet another embodiment, a base layer 550 (corresponding to inner region 208 of FIG. 2) may be formed by spraying a preformed mandrel 552 with a solution 554 including a weldable polymer. The preformed mandrel 552 may comprise a moldable material, such as polyethylene terephthalate (PET) that has been blow molded or otherwise formed into the desired configuration using conventional techniques. Solution 554 may consist of a nylon soluble in an alcohol or a similar solvent. During the spraying process, mandrel 552 may be indexed past spray head or nozzle 556 or the nozzle may be indexed along the length of the mandrel to control the amount and rate of application of solution 554 to the mandrel in different areas of the mandrel corresponding to the neck, cone and barrel section of the finished balloon. Mandrel 552 may be rotated or spun as indicated by arrow 558 during and/or after the spraying operation to insure that the mandrel is uniformly coated with solution 554.

Multiple layers of sprayed on solution 554 may be applied during the process in order to achieve the desired thickness of base layer 550. After the desired amount of solution 554 has been applied, mandrel 552 may be placed in an oven to promote drying and/or curing of the solution to complete formation of the base layer. The heating process may also be carried out between successive applications of solution 554. In different variations of the method, solution 554 may be sprayed onto the balloon lay up at various stages during the construction of the balloon to provide additional thermally weldable material to the lay up and/or provide to provide a "tacky" surface to which additional materials may be applied. For example, in one embodiment, solution 554 may be applied over tape 522 (FIGS. 5D and 5F) to provide a "tacky" surface.

Figure 5H:
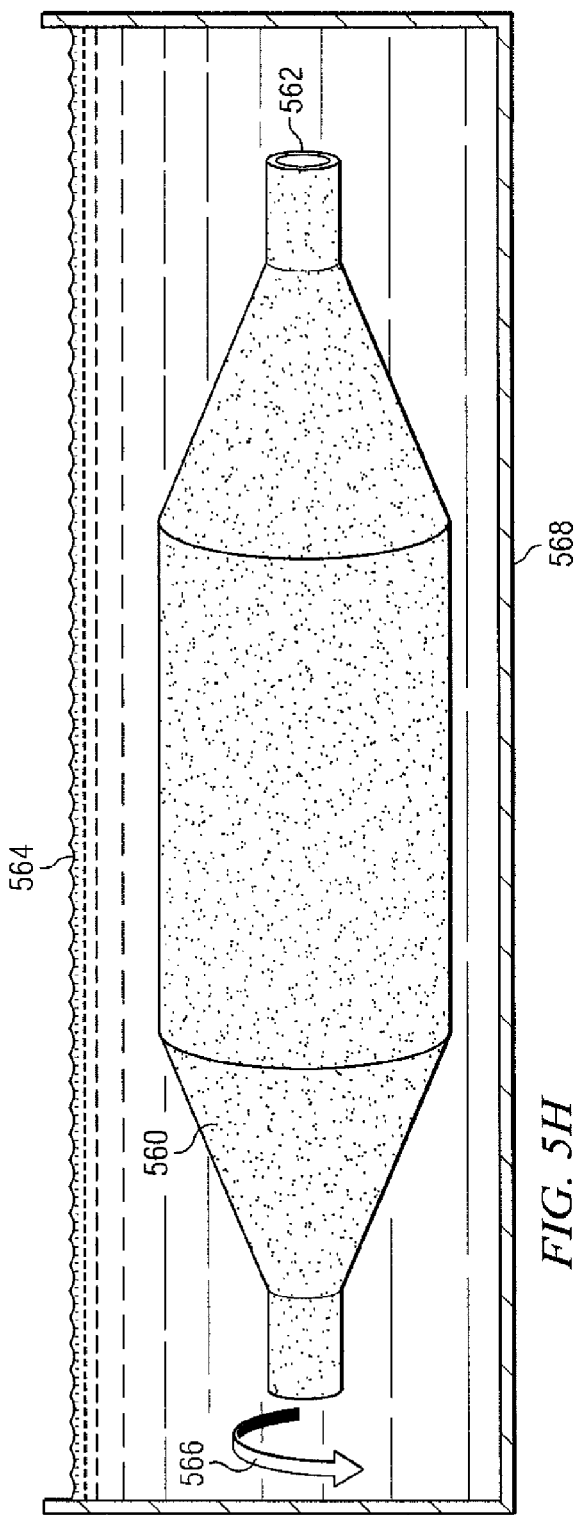
FIG. 5H illustrates a method of forming a base layer or inner layer on a preformed mandrel by means of immersing the mandrel in a solution including a thermally weldable material to coat the mandrel with the material.

Turning to FIG. 5H, in yet another embodiment, a base layer 560 (corresponding to inner region 208 of FIG. 2) may be formed by dipping or immersing a mandrel 562 in a solution 564 including a thermally weldable polymer. Solution 564 may consist of a nylon, for example nylon 6, nylon 6.6, nylon 11 or nylon 12 soluble in an alcohol or a similar solvent. During the coating process, mandrel 562 may be rotated or spun as indicated by arrow 566 during and/or after the dipping operation to insure that the mandrel is uniformly coated with solution 564. In some variations, mandrel 562 may be placed in tank 568 to coat the mandrel with solution 564, then withdrawn from the tank and rotated to insure a uniform coating.

Referring still to FIG. 5H, mandrel 562 may be dipped in solution 564 multiple times in order to achieve the desired thickness of base layer 560. After mandrel 562 has been dipped in tank 568, the coated mandrel may be heated, for example placed in an oven, to promote drying and/or curing of the solution to complete formation of the base layer. The heating process may also be carried out between successive dipping of mandrel 562 in solution 564. In different variations of the method, the balloon lay up may be immersed or dipped in solution 564 at various stages during the construction of the balloon to provide additional thermally weldable material to the lay up and/or provide to provide a "tacky" surface to which additional materials may be applied.

Figure 5I:
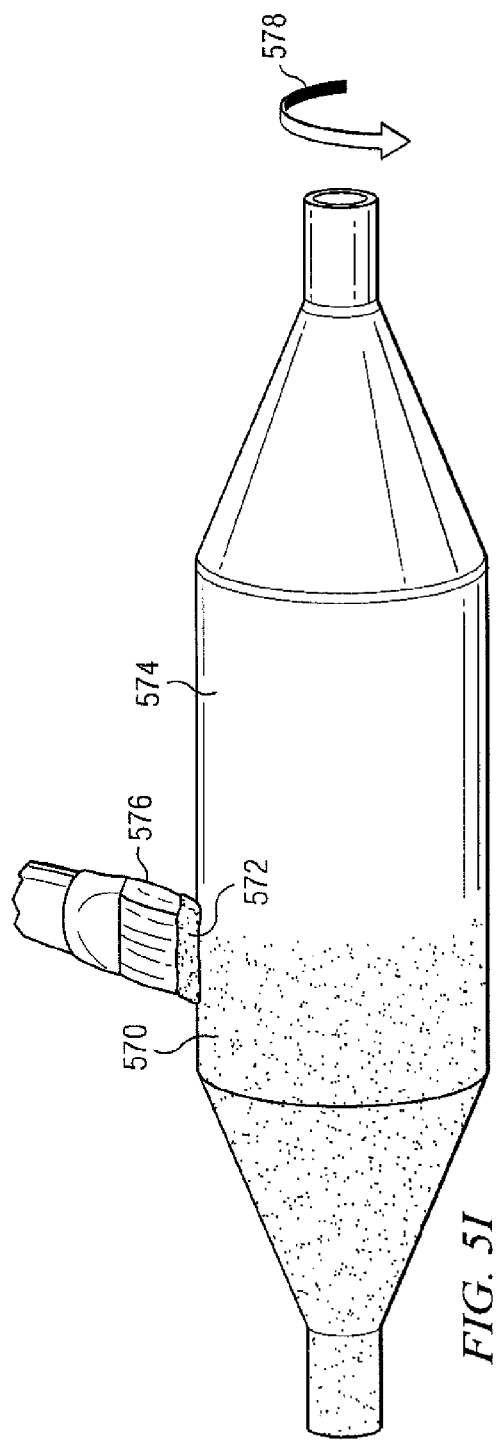
FIG. 5I illustrates a method of forming a base layer or inner layer on a preformed mandrel by means of brushing a solution including a thermally weldable material onto the mandrel.

Turning to FIG. 5I, in yet another embodiment, a base layer 570 (corresponding to inner region 208 of FIG. 2) may be formed by applying a solution 572 including a thermally weldable polymer to a mandrel 574 with a brush 576. The brushing process may be done manually or with an automated machine. During the brushing process, mandrel 574 may be rotated as indicated by arrow 578 in a fixture to facilitate uniform application of solution 572 to the mandrel. In other embodiments, solution 572 may be brushed onto the balloon lay up or other layers of materials to provide a "tacky" surface to which additional materials may be applied as the balloon is constructed. For example, solution 572 may be brushed over a preformed or formable mandrel wrapped with a tape of thermally weldable material (FIGS. 5D and 5F).

Figure 6:
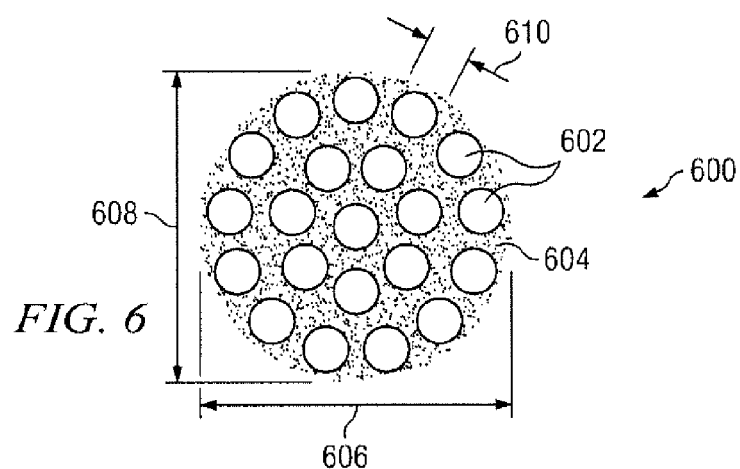
FIG. 6 is a cross-sectional end view of a tow of inelastic fiber material prior to flattening.

Referring now to FIG. 6, the inelastic fiber material used to make the reinforcing fibers 202 and 204 of balloon 100 may originally be provided in the form of a bundle or "tow" 600 of individual filaments 602. An adhesive or gel 604 may be included between the filaments 602 to help maintain the shape of the tow 600. The tow may have a generally circular cross-section with a width 606 and thickness 608 substantially equal to one another and substantially greater than the thickness 610 of an individual filament 602. The inelastic fiber material used to make fibers 202 and 204 of balloon 100 is capable of withstanding heating to 3000 F to 3500 F while retaining at least 95% of the tensile strength of the fibers.

Figure 7:
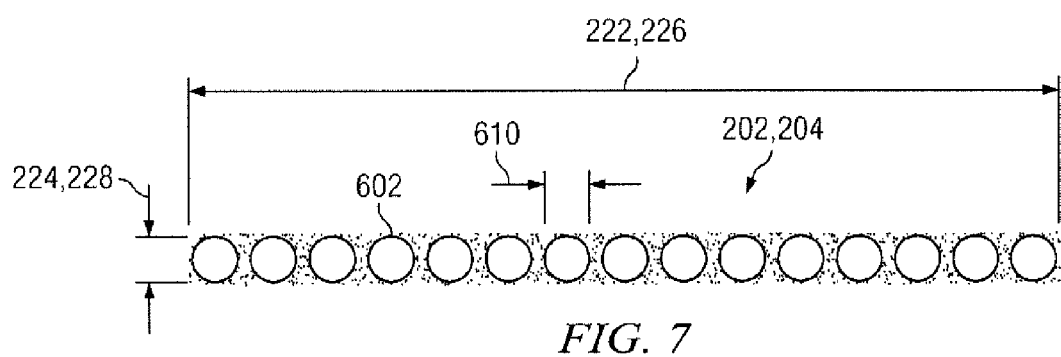
FIG. 7 is a cross-sectional end view of a flattened tow of inelastic fiber material used as a reinforcing fiber in some embodiments.

Referring now to FIG. 7, there is illustrated a tow of inelastic fiber material that has been modified to form reinforcing fibers 202, 204 having a flattened cross-section. In preferred embodiments, the thickness 224, 228 of the fibers 202, 204, respectively, may be within the range of about 1 to 2 times the thickness 610 of an individual filament 602. For example, Technora® brand para-aramid fiber having an original tow thickness 608 of about 0.003 inches and a filament thickness 610 of about 0.0005 inches may be flattened to form reinforcing fibers 202, 204 having a thickness 224, 228 of about 0.0005 inches and a width 222, 226 of about 0.015 inches.

Referring now to FIG. 8, one process for forming the flattened reinforcing fibers 202, 204 is illustrated. The original tow 600 of inelastic fiber is unreeled from a supply drum 800 and squeezed between one or more sets of closely spaced-apart rollers 802. A solvent or solvent-based adhesive may be applied to the tow 600 at a wetting-station 804 to remove or soften the original adhesive/gel 604 and facilitate rearrangement of the filaments 602 within the tow. The spacing between the final set of rollers 802 controls the thickness of the reinforcing fiber 202, 204. After leaving the final set of rollers 802, the fibers 202, 204 may be dried, if necessary, and then used immediately or stored for later processing.

Referring still to FIG. 8, one process for forming the so-called sock (i.e., the pre-formed sheet incorporating the longitudinal reinforcing fibers 202) begins by winding the flattened fiber 202 onto a sock drum 806 at a predetermined pitch (i.e., distance between successive fiber positions) 808. In the illustrated embodiment, the flattened fiber 202 is wound onto the sock drum 806 directly after leaving the flattening rollers 802, however, in other embodiments the fiber 202 may be processed earlier and provided from a storage roll (not shown). The pitch 808 between successive winds of fiber 202 may be produced by moving the sock drum 806 laterally (denoted by arrow 810) while winding or by moving the fiber feed laterally across the sock drum while winding. In some embodiments, the pitch 808 is selected to provide a spacing (i.e., spacing=pitch minus fiber width) between winds that is less than one fiber width 222. In preferred embodiments, the pitch 808 is selected to provide spacing between winds that is less than 50% of the fiber width 222, and in more preferred embodiments, the pitch is selected to provide spacing between winds that is less than 25% of the longitudinal fiber width. For example, in one embodiment having longitudinal fibers 202 with width 222 of about 0.015 inches, the pitch 808 is about 66 TPI (threads per inch), leaving a space of only about 0.0002 inches between fibers.

Prior to winding the longitudinal reinforcing fibers 202 onto the sock drum 806, a layer of anti-stick/protective material 812 may be applied to the drum surface. In one embodiment, the anti-stick/protective materials 812 is a layer of Teflon® brand tape wrapped around the drum 806. The anti-stick/protective material 812 protects the fibers 202 from the drum and facilitates release of the sock from the drum after processing.

Referring now to FIG. 9, after winding the reinforcing fibers 202 onto the drum 806, a sock coating 900 of thermally-weldable polymer material 902 may be applied across the fibers and surface of the drum. The sock coating 900 is preferably applied by spraying, but may be applied by brushing, dipping or other means. The sock coating 900 will ultimately become the sock region 212 of the matrix 206; therefore, it must be compatible for thermal-welding to the other materials in the matrix. In one embodiment, the sock coating 900 may be formed of a soluble nylon material having a thickness of about 0.0003 inches. In an alternative embodiment (not shown) the sock coating 900 is applied directly to the surface of the sock drum 806 (or, if present, to the anti-stick/protective material 812) before winding on the reinforcing fibers 202. In one such alternative embodiment, the sock coating 900 may be formed of a soluble nylon material having a thickness of about 0.0003 inches.

Referring now to FIG. 10, after applying the sock coating 900 to the longitudinal fibers 202 (or vice-versa) and allowing it to dry, the resulting sock sheet 1000 is cut and removed from the drum 806. The sock sheet 1000 now comprises a plurality of substantially parallel reinforcing fibers 202 affixed to a film of thermally-weldable polymer material 902 (from the sock coating 900).

Referring now to FIG. 11, the sock sheet 1000 is pressed and heated to smooth its surfaces and firmly embed the reinforcing fibers 202 into the thermally-weldable matrix material 902. In one embodiment, the sock sheet 1000 is placed between two flat steel sheets 1100, clamped together, and heated in an oven (not shown). In another embodiment, wherein the reinforcing fibers 202 are Technora® brand para-aramid fibers approximately 0.0005 inches thick, and the thermally-weldable material 902 is nylon, the sock sheet is heated between flat steel sheets at 250 degrees F. for a period within the range of about 20 to 30 minutes. During the pressing/heating procedure, the matrix material 902 may plastically deform such that, after cooling, the sheet is perfectly smooth and has the thickness of the reinforcing fibers 202.

Referring now to FIGS. 12, 13, and 13A-H, the finished sock sheet 1000 is next patterned and cut to shape. A flat pattern 1200 may be created corresponding to the outer wall of the balloon 100, wherein the pattern represents the three-dimensional outer surface of the balloon that has been cut along lines parallel to the longitudinal axis 108 and "unfolded" into a two-dimensional (i.e., flat) surface. The pattern 1200 will have a pattern axis 1202 corresponding to a line on the surface of the balloon 100 that is parallel to the longitudinal axis 108. In the illustrated embodiment, the pattern 1200 may correspond to the entire outer wall of the balloon 100 (including the barrel wall 114, cone walls 116 and neck walls 122). In another embodiment, the pattern 1200 may correspond to selected portions of the outer wall of the balloon 100. In preferred embodiments, the pattern 1200 will correspond to portions of the surface of the balloon extending longitudinally along the entire length of the balloon, i.e., from the outer end of one neck to the outer end of the opposite neck.

Referring now specifically to FIG. 12, for purposes of illustration the reinforcing fibers 202 may be shown in FIG. 12 as having an abbreviated length in order to more clearly show the pattern 1200, however it will be understood that the fibers 202 may actually run across the entire length of the sock sheet 1000 as shown in FIG. 11. The pattern 1200 may be superimposed on the sock sheet 1000 with the pattern axis 1202 oriented substantially parallel to the reinforcing fibers 202. This may ensure that the longitudinal reinforcing fibers 202 run substantially parallel to the longitudinal axis 108 in the finished balloon 100. The pattern 1200 may then be cut out of the sock sheet 1000 to form the final patterned sock 1300. In one embodiment, the pattern 1200 may be transferred to the surface of the sock sheet 1000 (e.g., by printing) and the patterned sock 1300 may be cut out by hand (e.g., by knife, scissors, etc.). In another embodiment, the pattern 1200 may be incorporated into the shape of a cutting tool (e.g., a cutting die or cutting punch) and the patterned sock 1300 may be cut from the properly oriented sock sheet 1000 by an automated cutting apparatus (e.g., a die cutting machine) using the cutting tool. In yet another embodiment, the pattern 1200 may be incorporated into a computer program or set of CNC instructions and the patterned sock 1300 may be cut from the properly oriented sock sheet 1000 by a computer-controlled/CNC cutting apparatus, e.g., a laser cutter 1204 (shown in FIG. 12), a water jet cutter or numerically-controlled knife.

Referring now specifically to FIG. 13, the finished patterned sock 1300 may include barrel, cone and neck portions 1302, 1304 and 1306, respectively corresponding to the barrel, cone and neck portions 102, 104 and 106 of the finished balloon 100. In the finished patterned sock 1300, selected reinforcing fibers 202 may extend continuously from one longitudinal end of the patterned sock to the opposite longitudinal end. For example, in the embodiment illustrated in FIG. 13, reinforcing fiber 202*a* extends continuously from neck portion 1306*a* at one longitudinal end of the patterned sock to neck portion 1306*b* at the opposite longitudinal end.

Figure 13A:
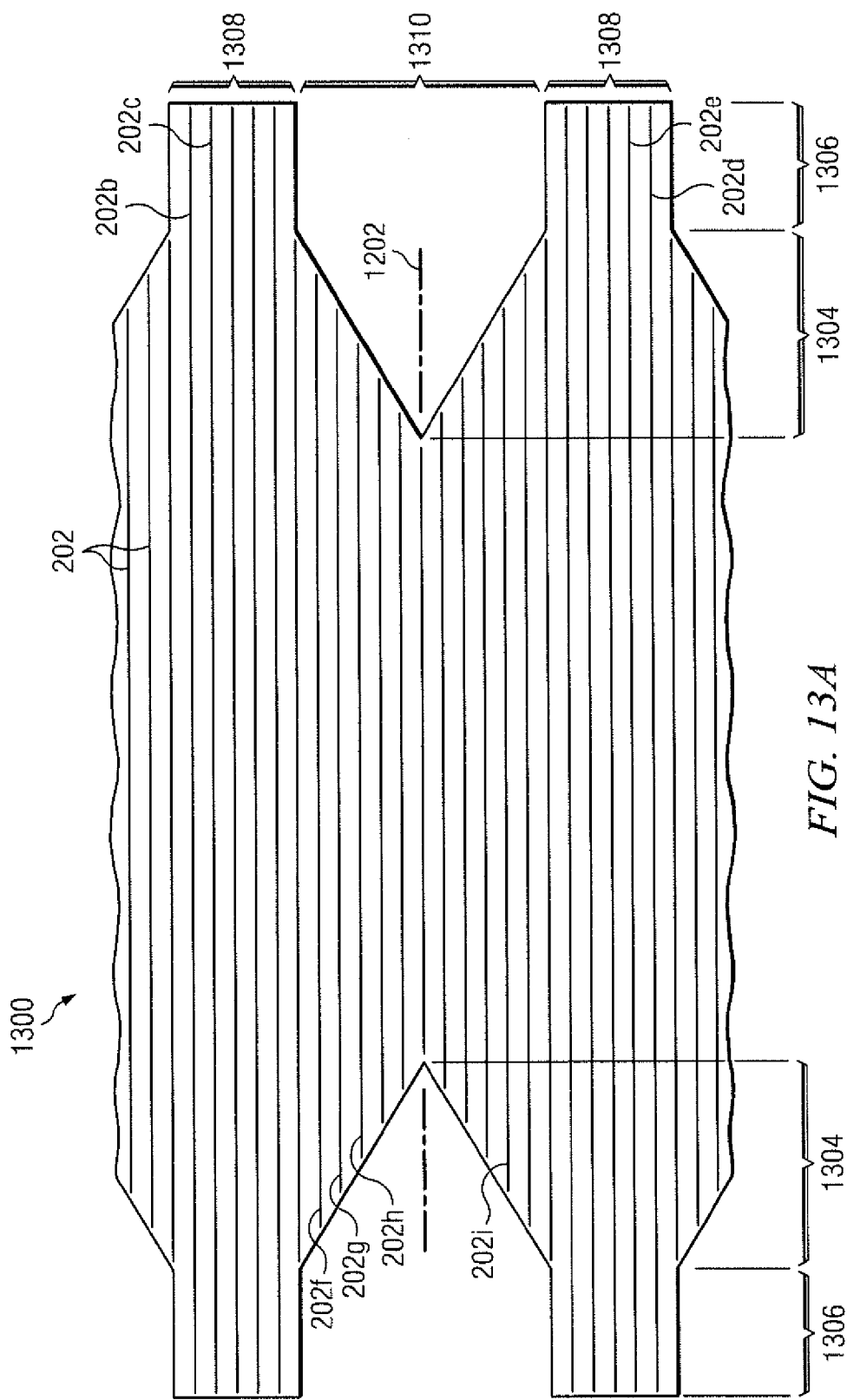
FIG. 13A shows an enlarged view of a portion of the patterned sock of FIG. 13 to better illustrate the pattern of the reinforcing fibers.

Referring now specifically to FIG. 13A, an enlarged portion of the patterned sock 1300 is shown to better illustrate the pattern of the reinforcing fibers 202 within the sock. It will be understood that outline of the sock shown in FIG. 13A is for purposes of illustration and is not intended to show the exact shape necessary to cover the balloon shown in FIG. 1. As previously described, the fibers 202 of the patterned sock 1300 may run substantially parallel to one another and substantially parallel to the sock axis 1202 that may be aligned with the longitudinal axis 108 of the balloon. The fibers 202 in the sock may have a pattern of different lengths such that the fibers may be divided into a first group and a second group based on length. The first group may be termed the "neck group" (denoted by reference number 1308 in FIG. 13A) and the second group may be termed the "cone group" (denoted by reference number 1310).

Each fiber of the neck group 1308 begins in the neck wall portion 1306 at one end of the sock, extends continuously in the longitudinal direction and terminates in the neck wall portion at the opposite end of the sock. The fibers denoted 202*b*, 202*c*, 202*d* and 202*e* are examples of fibers in the neck group 1308. Substantially all of the fibers 202 in the neck group 1308 have a generally uniform length.

Each fiber of the cone group 1310 begins in the cone wall portion 1304 at one end of the sock, extends continuously in the longitudinal direction and terminates in the cone wall portion at the opposite end of the sock. The fibers denoted 202*f*, 202*g*, 202*h* and 202*i* are examples of fibers in the cone group 1310. In contrast to the previous group, the length of the fibers 202 of the cone group 1310 varies progressively in accordance to their proximity to the fibers of the neck group 1308. The fibers of the cone group closer to the fibers of the neck group are longer than the fibers of the cone group further from the fibers of the neck group. Accordingly, fiber 202*f*, which is closest to the neck group 1308, is the longest of the example fibers, while fiber 202*h*, which is farthest from the neck group, is the shortest of the example fibers. Fiber 202*g*, disposed between fibers 202*f* and 202*h*, has an intermediate length. Fiber 202*i* has a length approximately equal to that of fiber 202*g*, because each is approximately the same distance from a neck group 1308.

Figure 13B:
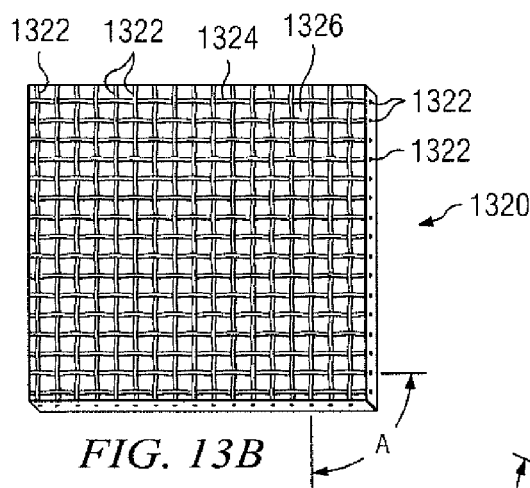
FIG. 13B shows an enlarged view of a portion of sock sheet similar to the sock of FIG. 13, but incorporating woven textile reinforcement in accordance with an alternate embodiment.

Turning to FIG. 13B, in an alternative embodiment, a sock sheet 1320 may be reinforced by weaving fibers 1322 into a woven textile material 1324. The woven textile material 1324 has a structure wherein fibers or filaments are interlaced. Fibers 1322 may be flattened prior to weaving as described above, or the woven textile material 1324 may be pressed, for example between rollers to achieve the desired thickness. In this variation, woven textile material 1324 may be coated with a thermally-weldable polymer material 1326, as described in connection with FIG. 9. After the coating has been applied, the sock sheet 1320 may be clamped between plates and heated to embed the fibers 1322 within the thermally-weldable polymer 1326 and produce a sheet 1320 having smooth surfaces. Alternatively, a film formed from a thermally-weldable polymer material may be placed over woven textile material 1324 prior to heating to form a sock sheet 1320. Fibers 1322 may form angles (denoted "A") at the intersections thereof that remain constant when a balloon incorporating sock material 1320 is inflated and deflated.

After embedding, the finished sock sheet 1320 formed using woven textile material 1324 may then be patterned and cut to shape as described above. For purposes of illustration, the weave of textile material 1324 is shown with a high porosity, i.e., a relatively large amount of open space between fibers 1322. Other woven textile fabrics having greater or lesser porosities, including those having a very tight weave with essentially no porosity may be used in other embodiments.

Figure 13C:
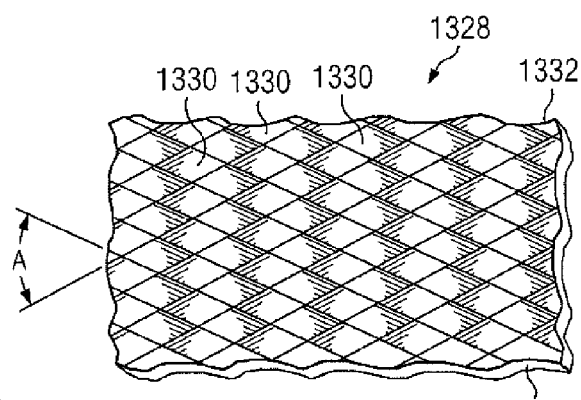
FIG. 13C shows an enlarged view of a portion of sock sheet similar to the sock of FIG. 13, but incorporating braided textile reinforcement in accordance with an alternate embodiment.

FIG. 13C illustrates another alternative embodiment, wherein a reinforced sock sheet 1328 may be reinforced by braiding fibers 1330 into a braided textile fabric 1332. A braided fabric 1332 employs a fiber architecture in which three or more fibers are intertwined in such a way that no two fibers are twisted exclusively around one another. Since all of the fibers 1332 within a braided structure are continuous and mechanically locked, a braid has a natural mechanism that evenly distributes load throughout the structure. Braided textile fabric 1332 is formed from fibers 1330 that may be flattened before braiding. Alternatively, braided textile material 1332 may be otherwise processed to achieve the desired thickness. Braided textile material 1332 may be coated with a thermally-weldable polymer material 1326 and heated as described above to embed fibers 1330 within the thermally-weldable polymer to produce a sock sheet 1328 having uniform smooth surfaces. Alternatively, a film formed from a thermally-weldable polymer material 1326 may be placed over braided textile material 1332 prior to heating to form a sock sheet 1328. The finished sock sheet 1328 may then be patterned and cut to shape. After fibers 1330 have been embedded in the thermally-weldable polymer 1326, the angles (denoted "A") between the fibers preferentially remain constant when a balloon incorporating sock sheet 1328 is inflated and deflated.

Figure 13D:
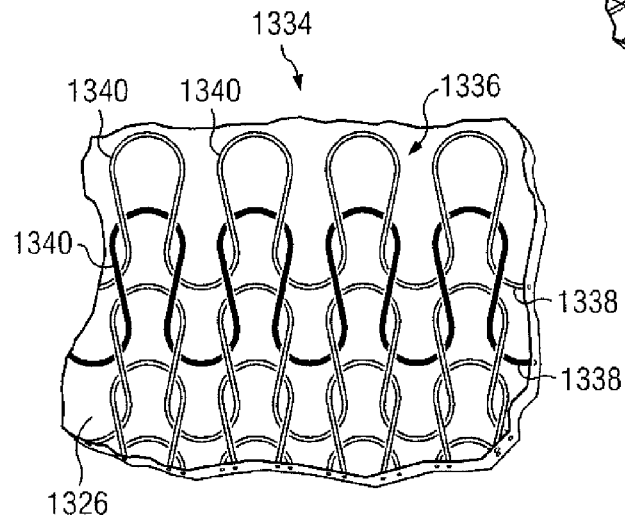
FIG. 13D shows an enlarged view of a portion of sock sheet similar to the sock of FIG. 13, but incorporating knitted textile reinforcement in accordance with an alternate embodiment.
Figure 13E:
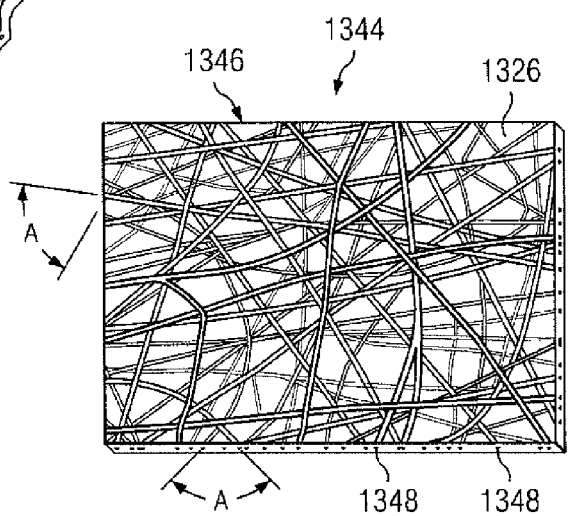
FIG. 13E shows an enlarged view of a portion of sock sheet similar to the sock of FIG. 13, but incorporating non-woven textile reinforcement in accordance with an alternate embodiment.

FIGS. 13D and 13E illustrate additional embodiments, wherein reinforced sock sheets 1334 and 1344 are reinforced by knitted textile material 1336 and non-woven textile material 1346, respectively. A knitted textile fabric is produced by intertwining fibers 1338 in a series of interconnected loops 1340 rather than by weaving. In this fashion, the loops 1340 of fibers 1338 are mechanically interlocked. A weft-knitted structure consists of horizontal, parallel courses of fibers and requires only a single fiber 1338. Alternatively, warp knitting requires one fiber 1338 for every stitch in the course, or horizontal row; these fibers make vertical parallel wales. In contrast, non-woven textile fabrics 1346 are typically made from randomly-oriented fibers that are neither woven nor knitted. The fibers 1348 in non-woven fabrics typically have a web structure in which small fibers or filaments are held together by inter-fiber friction (e.g., matting), thermal binding (e.g., with a meltable binder) or chemical adhesion.

Knitted textile material 1336 or non-woven textile material 1346 may be embedded in a thermally-weldable polymer 1326 as described above, cut and patterned to form a patterned sock material 1334 or 1344 similar to that shown in FIG. 13. In the case of the non-woven textile fabric 1346, the fibers 1348 may be randomly oriented, chopped fibers of the same or varying lengths that form random angles (denoted "A") at each fiber intersection. After the knitted fiber loops 1340 or non-woven fibers 1348 are embedded in the thermally-weldable polymer 1326, the relative positions of the loops 1340 or angles A between fibers preferably remains constant when a balloon incorporating sock sheet 1334 or 1344 is inflated and deflated.

Figure 13F:
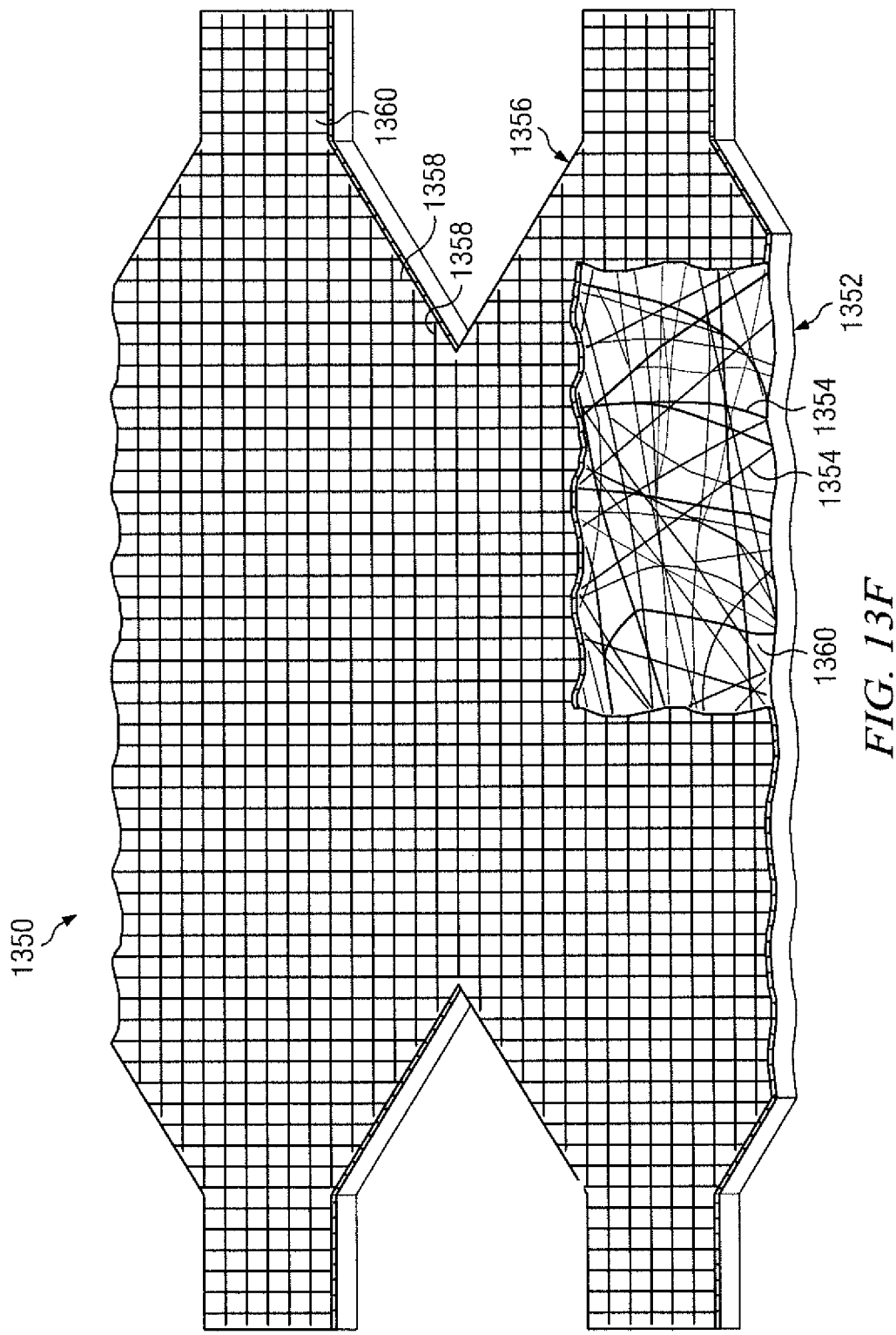
FIG. 13F shows a portion of a patterned sock including multiple textile reinforcement layers in accordance with another embodiment.
Figure 13H:
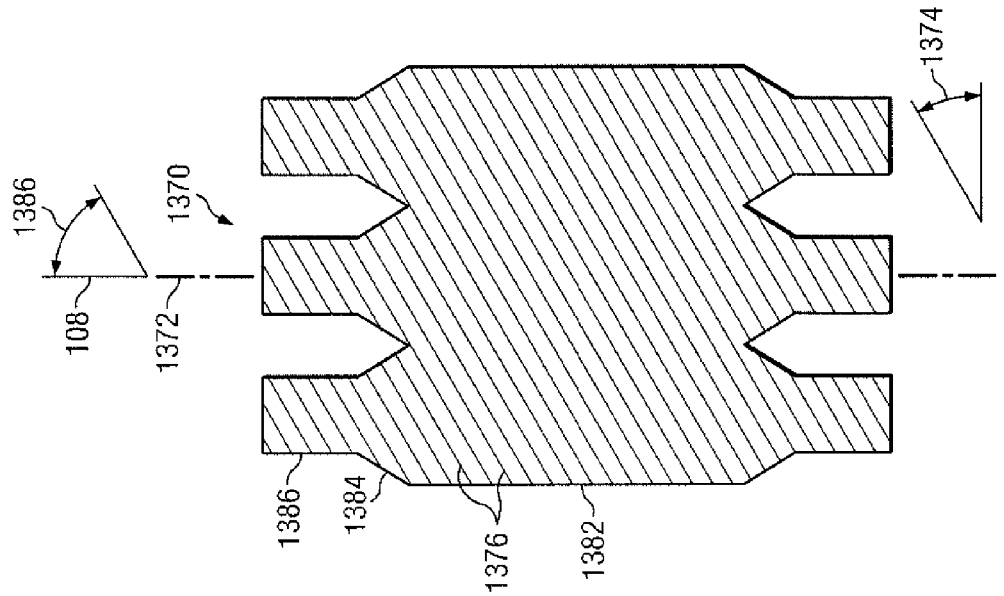
FIG. 13H shows a portion of the patterned sock of FIG. 13G further illustrating the pattern of the fibers in this embodiment.
Figure 13G:
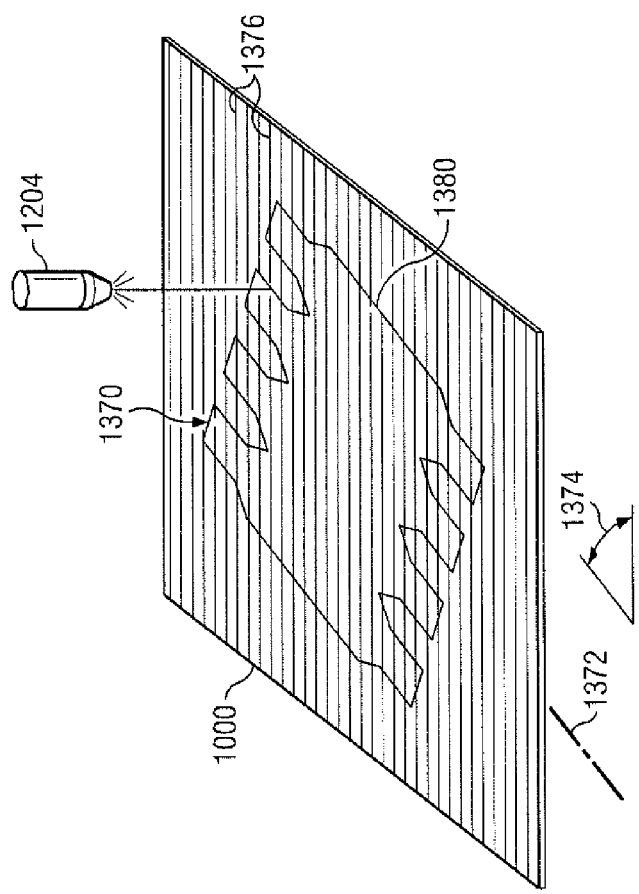
FIG. 13G illustrates patterning and cutting a pre-fabricated fiber-reinforced balloon wall layer in accordance with additional embodiments.

Referring to FIGS. 13G and 13H, in one embodiment a patterned sock 1370 may be formed or cut from a sock sheet, such as sock sheet 1000 of FIGS. 11 and 12 with the pattern axis 1372 (i.e., corresponding to a line on the surface of the balloon that is parallel to the longitudinal axis of the finished balloon) oriented at an angle 1374 substantially less than perpendicular relative to the orientation of fibers 1376. In this variation, a pattern 1380 may be superimposed on the sock sheet 1000 with the pattern axis 1372 oriented at an angle 1372, for example 30, 45 or 60 degrees, relative to reinforcing fibers 1376. The pattern 1380 may be superimposed on sheet 1000 and cut from the by hand, with a cutting die or punch or with a computer-controlled/CNC cutting apparatus such as a laser cutter 1204, a water jet cutter or numerically-controlled knife.

As best illustrated in FIG. 13H, the cut patterned sock 1300 may include barrel sections 1382, cone sections 1384 and neck sections 1385, corresponding to the barrel, cone and neck portions 102, 104 and 106 of the finished balloon 100. In this embodiment, reinforcing fibers 1376 may extend generally parallel to adjacent reinforcing fibers in a helical pattern over the length of the balloon from one longitudinal end of patterned sock 1370 to the opposite longitudinal end of the patterned sock. Thus, when balloon 100 is assembled, reinforcing fibers 1376 of the patterned sock 1370 may run substantially parallel to one another and at an angle substantially less than perpendicular to the longitudinal axis 108 (FIG. 1) of the balloon. For example, in various embodiments, the angle 1376 between the longitudinal axis 108 of the balloon 100 and reinforcing fibers 1376 may range from greater than 25 degrees to less than 70 degrees. In other embodiments, angle 1386 may range from between about 30 degrees to about 60 degrees.

The textile fabrics illustrated in FIGS. 13B-13E may be formed from a variety of substantially inelastic polymers. For example, Kevlar, Vectran, Spectra, Dacron, Dyneema, Turlon (PBT), Zylon (PBO), polyimide (PIM) and other ultrahigh molecular weight polyethylenes, aramids, and similar polymers may be used to manufacture the fibers.

Referring now to FIG. 13F, in another variation, multiple textile reinforcing layers may be used to form a patterned sock 1350. In the illustrated embodiment, patterned sock 1350 is formed from a first non-woven textile layer 1352 having randomly oriented fibers 1354 and a second textile layer 1356 formed from woven fibers 1358. For purposes of illustration, portions of the sock 1350 are broken away in FIG. 13F to show both reinforcing layers 1352 and 1356. One or both of textile layers 1352 and 1356 may be coated with a thermally-weldable polymer material 1360, or pressed together and heated to embed fibers 1354 and 1358 in a continuous polymer matrix. In other embodiments, layers of knitted, braided, woven, non-woven and patterned fabrics textiles and fibers may be combined to form patterned sock sheets.

Figure 14:
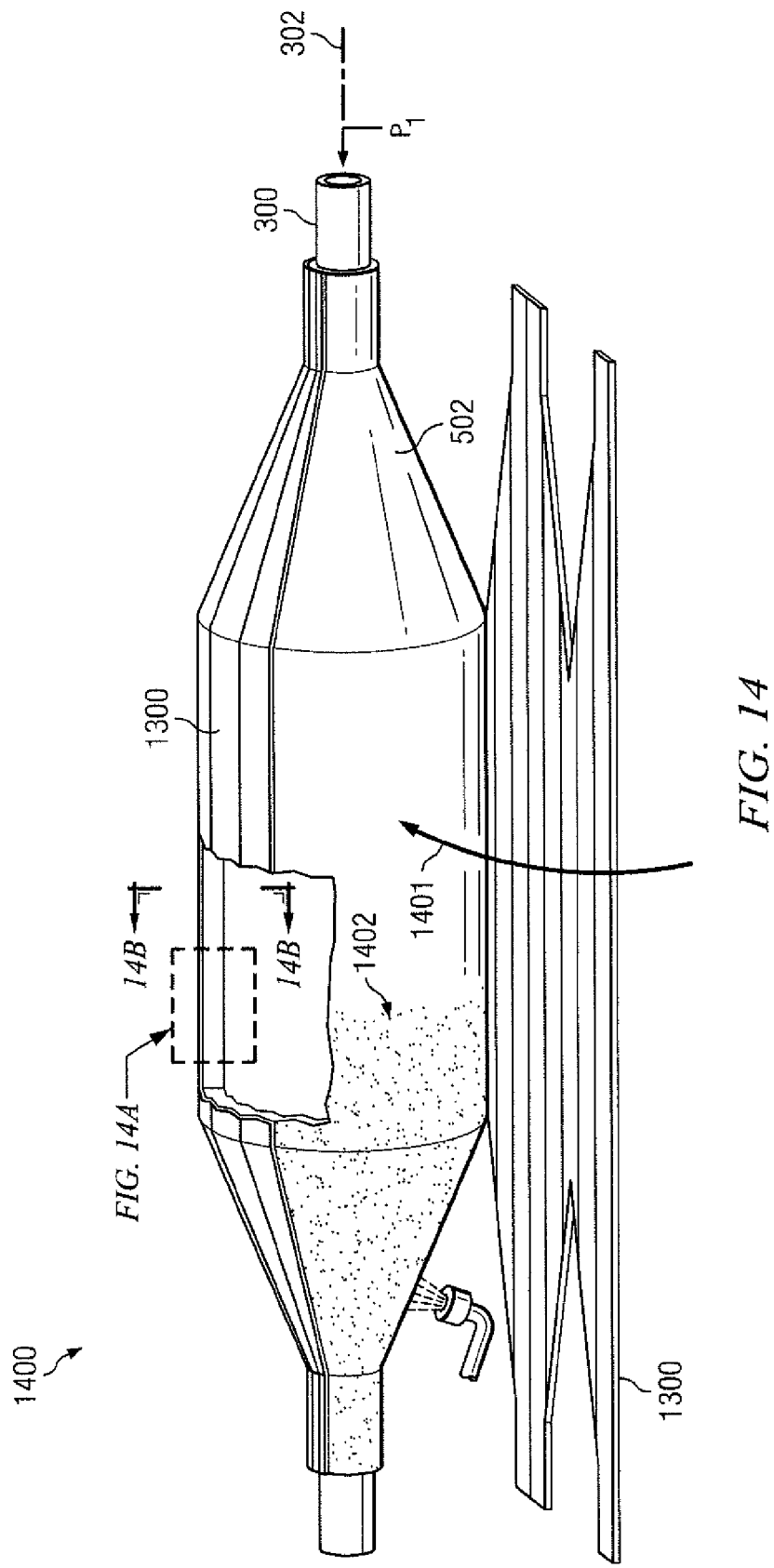
FIG. 14 illustrates affixing a patterned sock over the in-progress balloon and mandrel in accordance with additional embodiments.
Figure 14A:
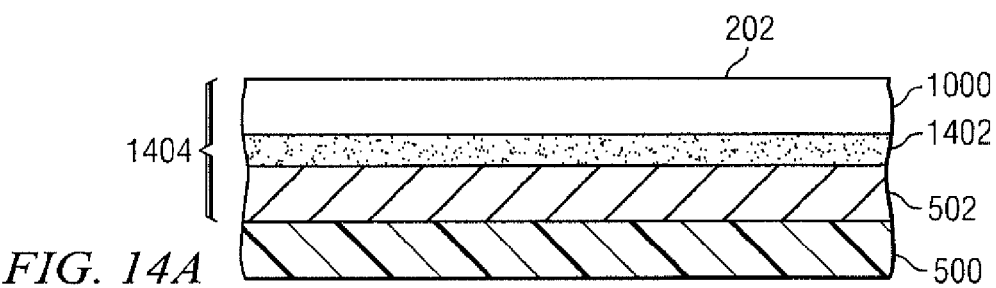
FIG. 14A is an enlarged cross-sectional view of the in-progress balloon wall overlying the mandrel looking in the circumferential direction taken along line 14A-14A of FIG. 14.
Figure 14B:
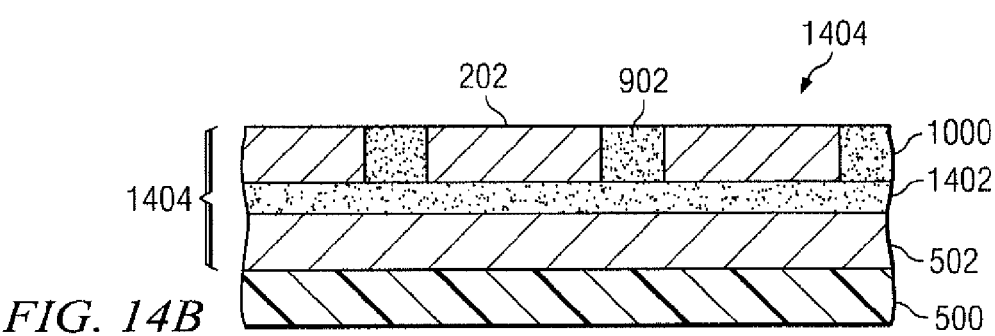
FIG. 14B is an enlarged cross-sectional view of the in-progress balloon wall overlying the mandrel looking in the longitudinal direction taken along line 14B-14B of FIG. 14.

Referring now to FIG. 14, 14A and 14B, the patterned sock 1300 (or alternatively, socks 1320, 1328, 1334, 1344 or 1350) may be affixed over the illustrated balloon lay-up 1400, which now comprises the conformal layer 502 covering the removable semi-compliant mandrel 500 (as seen in FIG. 5). The size and shape of the mandrel 500 is preserved during processing by maintaining a predetermined internal pressure $P_1$ via the tube 300. The patterned sock 1300 may be oriented such that the reinforcing fibers 202 are oriented parallel or substantially parallel to the longitudinal axis 302 of the mandrel 500 (which corresponds at this point to the longitudinal axis 108 of the final balloon 100). In some embodiments, the reinforcing fibers 202 are oriented within ±10 degrees of parallel to the longitudinal axis 302. In some embodiments, a one-piece patterned sock 1300 may be "rolled" (denoted by arrow 1401) onto the conformal layer 502 so as to cover the entire surface. Preferably, no adhesive materials are used to affix the patterned sock 1300 to the conformal layer 502.

The patterned sock 1300 will ultimately become the first layer 201 of longitudinally-oriented reinforcing fibers in the finished balloon 100. Embodiments in which the fibers 202 in the sock 1300 have a particular pattern may have a substantially similar pattern in the fibers of the first fiber layer 201 in the finished balloon 100. Embodiments in which the fibers 202 in the sock 1300 have a pattern of different lengths such that the fibers may be divided into a first group and a second group based on length may have a substantially similar pattern in the fibers of the first fiber layer 201 in the finished balloon 100. The thermally-weldable material in the sock sheet will become the sock region 212 of the matrix 206.

To facilitate attachment of the patterned sock 1300 to the conformal layer 502, in some embodiments a solvent compatible with the thermally-weldable material 902 of the sock sheet may be applied to "tackify" (i.e., to make slightly sticky or tacky) the inside surface of the patterned sock 1300. In other embodiments, a first coating 1402 of thermally-weldable material may be applied over the conformal layer 502 prior to affixing the patterned sock 1300. The first coating 1402 (if present) is preferably applied by spraying, but may be applied by brushing, dipping or other means. The first coating 1402 will ultimately become the first coating region 210 of the matrix 206, therefore it must be compatible for thermal-welding to the other materials in the matrix. In one embodiment the first coating 1402 may be formed of a soluble nylon material having a thickness of about 0.0003 inches. Such a first coating 1402 may be thermal-welding compatible with a conformal layer 502 when formed of PEBA such as Pebax®. It will be appreciated that the patterned sock 1300 may not be welded or permanently joined to the conformal layer 502 (or first coating 1402) at this time. It is only necessary that the patterned sock 1300 be affixed well enough to stay in position during further processing.

Referring now specifically to FIGS. 14A and 14B, after affixing the patterned sock 1300 over the conformal layer 502, the in-progress wall 1404 of the balloon 100 is illustrated on the outer surface of the mandrel 500. In the embodiment illustrated, the first coating 1402 has been applied as previously described.

Figure 15A:
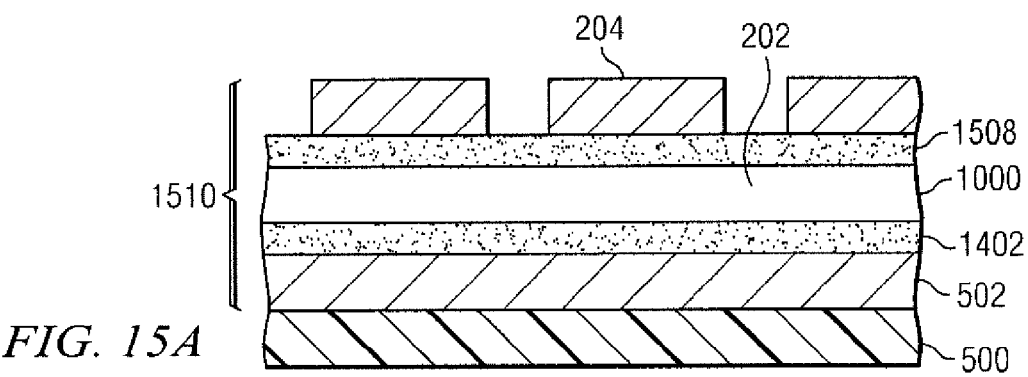
FIG. 15A is an enlarged cross-sectional view of the in-progress balloon wall overlying the mandrel looking in the circumferential direction taken along line 15A-15A of FIG. 15.
Figure 15B:
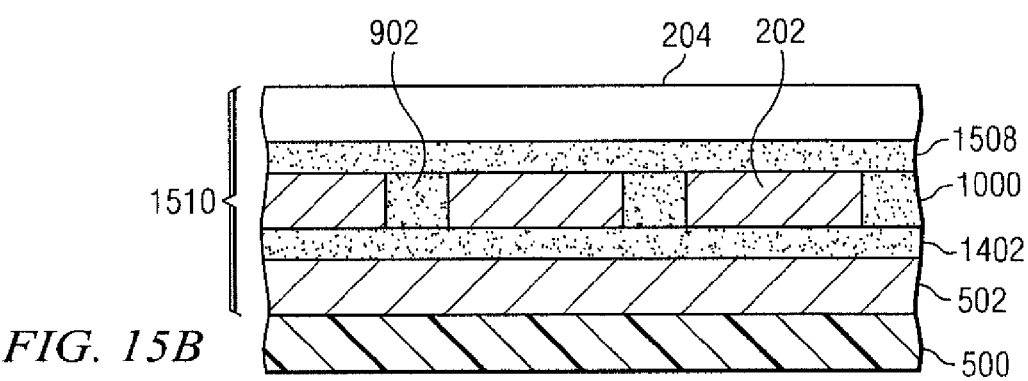
FIG. 15B is an enlarged cross-sectional view of the in-progress balloon wall overlying the mandrel looking in the longitudinal direction taken along line 15B-15B of FIG. 15.
Figure 15:
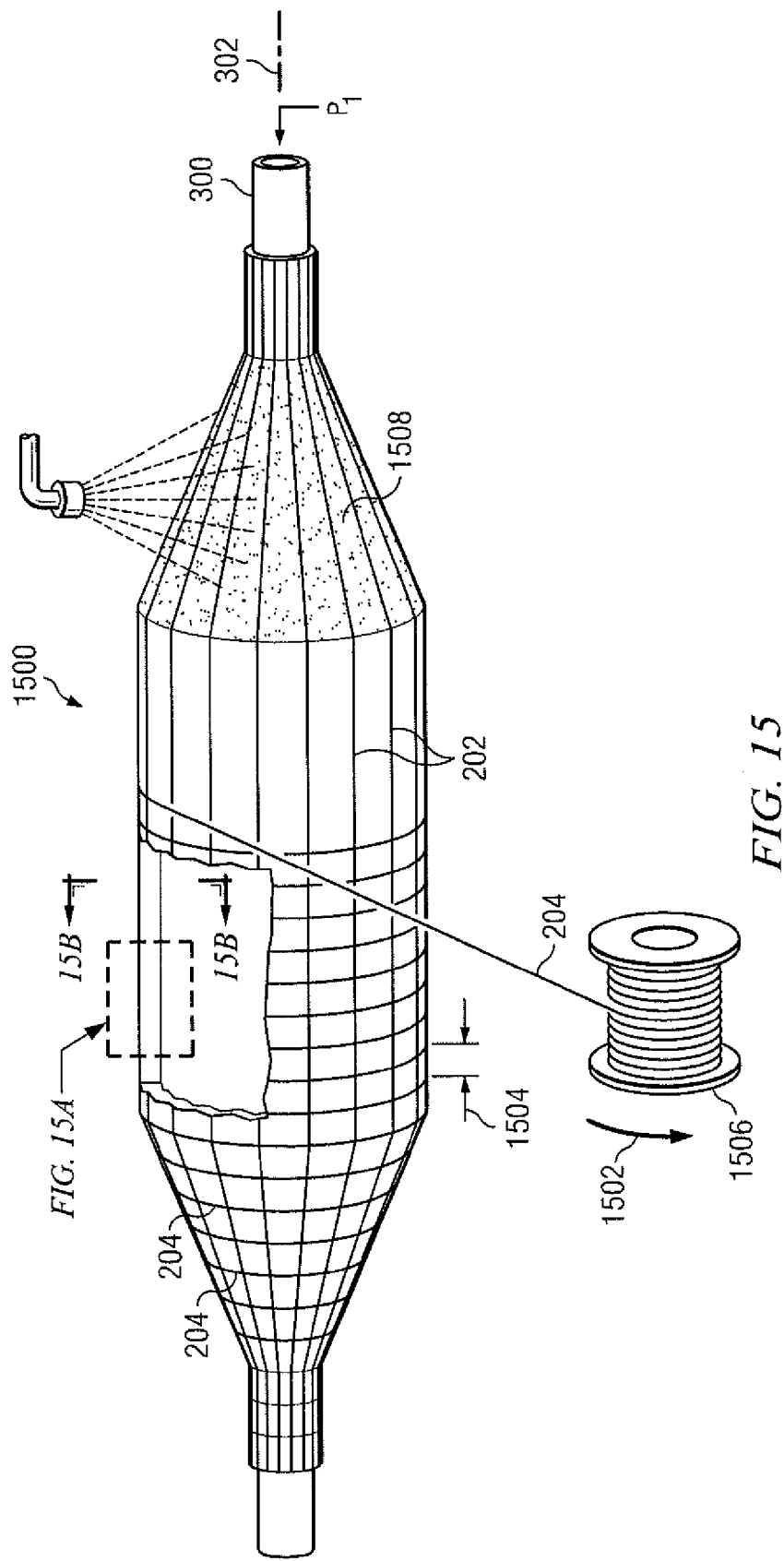
FIG. 15 illustrates winding circumferential "hoop" reinforcing fibers around the in-progress balloon and mandrel in accordance with additional embodiments.

Referring now to FIGS. 15, 15A and 15B, the hoop reinforcing fibers 204 may be affixed over the illustrated balloon lay-up 1500, which now includes the patterned sock 1300 with longitudinal reinforcing fibers 202. The balloon lay-up 1500 is supported by the underlying mandrel 500, which remains pressurized at the predetermined internal pressure $P_1$ to maintain its size and shape. The flattened hoop reinforcing fibers 204 may be wound circumferentially around the balloon lay-up 1500 at a predetermined pitch 1504 such that successive winds are oriented parallel or substantially parallel to one another and perpendicular or substantially perpendicular to the longitudinally-oriented reinforcing fibers 202. In some embodiments, the hoop fibers 204 are wound within ±10 degrees of perpendicular to the longitudinal reinforcing fibers 202

The flattened hoop fibers 204 may be supplied from a storage drum 1506 or other source. In preferred embodiments, the fibers 204 may be wound continuously around the balloon lay-up 1500 from one neck to the opposite neck. In the illustrated embodiment, the circumferential winding (denoted by arrow 1502) is accomplished by revolving the storage drum 1506 around the balloon lay-up 1500, however in other embodiments the balloon lay-up and mandrel 500 may be rotated. In some embodiments, the hoop pitch 1504 is selected to provide a spacing between hoop winds that is less than one hoop fiber width 226. In preferred embodiments, the pitch 1504 is selected to provide spacing between hoop winds that is less than 50% of the hoop fiber width 226, and in more preferred embodiments, the pitch is selected to provide spacing between hoop winds that is less than 25% of the hoop fiber width. For example, in one embodiment having hoop fibers 204 with width 226 of about 0.015 inches, the pitch 1504 is about 66 TPI (threads per inch), leaving a space of only about 0.0002 inches between hoop fibers.

Prior to winding the hoop reinforcing fibers 204 onto the balloon lay-up 1500, a second coating 1508 of thermally-weldable matrix material may be applied to the surface of the balloon lay-up to facilitate retention of the hoop fibers. In some embodiments, the second coating 1508 is applied only to the surface of the cone portions 104, since the tendency for the fibers 204 to slip is greatest on the angled surfaces of the cones. The second coating 1508 (if present) is preferably applied by spraying, but may be applied by brushing, dipping or other means. The second coating 1508 will ultimately become the second coating region 214 of the matrix 206, therefore it must be compatible for thermal-welding to the other materials in the matrix. In one embodiment, the second coating 1508 may be formed of a soluble nylon material having a thickness of about 0.0003 inches. Such a second coating 1508 may be thermal-welding compatible with the first coating 1402 when formed of soluble nylon and/or the conformal layer 502 when formed of PEBA such as Pebax®. It will be appreciated that the patterned sock hoop fibers 204 may not be welded or permanently joined to the balloon lay-up at this time. It is only necessary that the hoop fibers 204 be affixed firmly enough to stay in position during further processing.

Referring now specifically to FIGS. 15A and 15B, after affixing the hoop reinforcing fibers, the in-progress wall 1510 of the balloon 100 is illustrated on the outer surface of the mandrel 500. In the embodiment illustrated, the second coating 1508 has been applied as previously described.

Figure 16A:
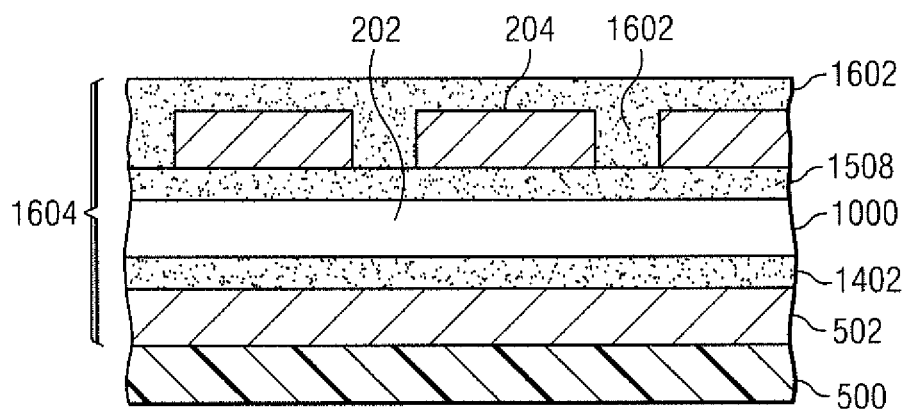
FIG. 16A is an enlarged cross-sectional view of the in-progress balloon wall overlying the mandrel looking in the circumferential direction taken along line 16A-16A of FIG. 16.
Figure 16B:
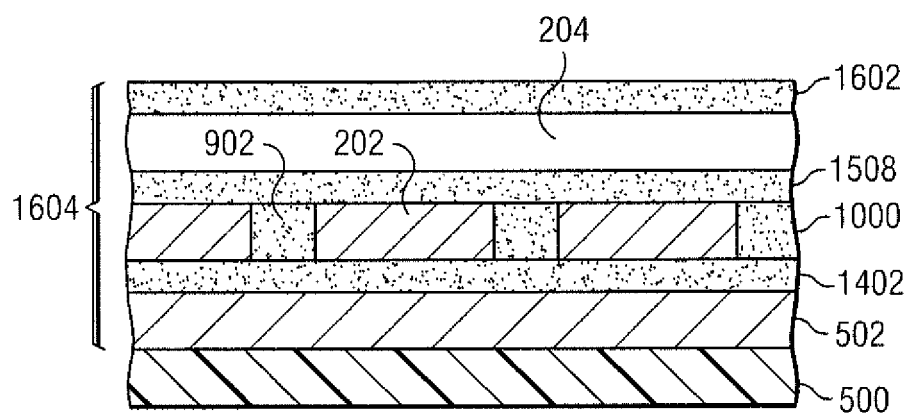
FIG. 16B is an enlarged cross-sectional view of the in-progress balloon wall overlying the mandrel looking in the longitudinal direction taken along line 16B-16B of FIG. 16.

Referring now to FIGS. 16, 16A and 16B, a third coating 1602 may be applied to the surface of the illustrated balloon lay-up 1600, which now includes both the hoop (i.e., circumferential) reinforcing fibers 204 and the longitudinal reinforcing fibers 202. The balloon lay-up 1600 is supported by the underlying mandrel 500, which remains pressurized at the predetermined internal pressure $P_1$ to maintain its size and shape. The third coating 1602 may facilitate holding the hoop fibers 204 in position and smoothing the surface of the balloon. In some embodiments, the third coating 1602 is applied to the entire surface of the balloon lay-up 1600. The third coating 1602 is preferably applied by spraying, but may be applied by brushing, dipping or other means. The third coating 1602 will ultimately become the third coating region 216 of the matrix 206, therefore it must be compatible for thermal-welding to the other materials in the matrix. In one embodiment, the third coating 1602 may be formed of a soluble nylon material having a thickness of about 0.0003 inches. Such a third coating 1602 may be thermal-welding compatible with the second coating 1508 (where present) when formed of nylon and with the thermally-weldable material 902 of the underlying sock sheet 1000 when formed of nylon.

Referring now specifically to FIGS. 16A and 16B, after applying the third coating 1602, the in-progress wall 1604 of the balloon 100 is illustrated on the outer surface of the mandrel 500.

Figure 17:
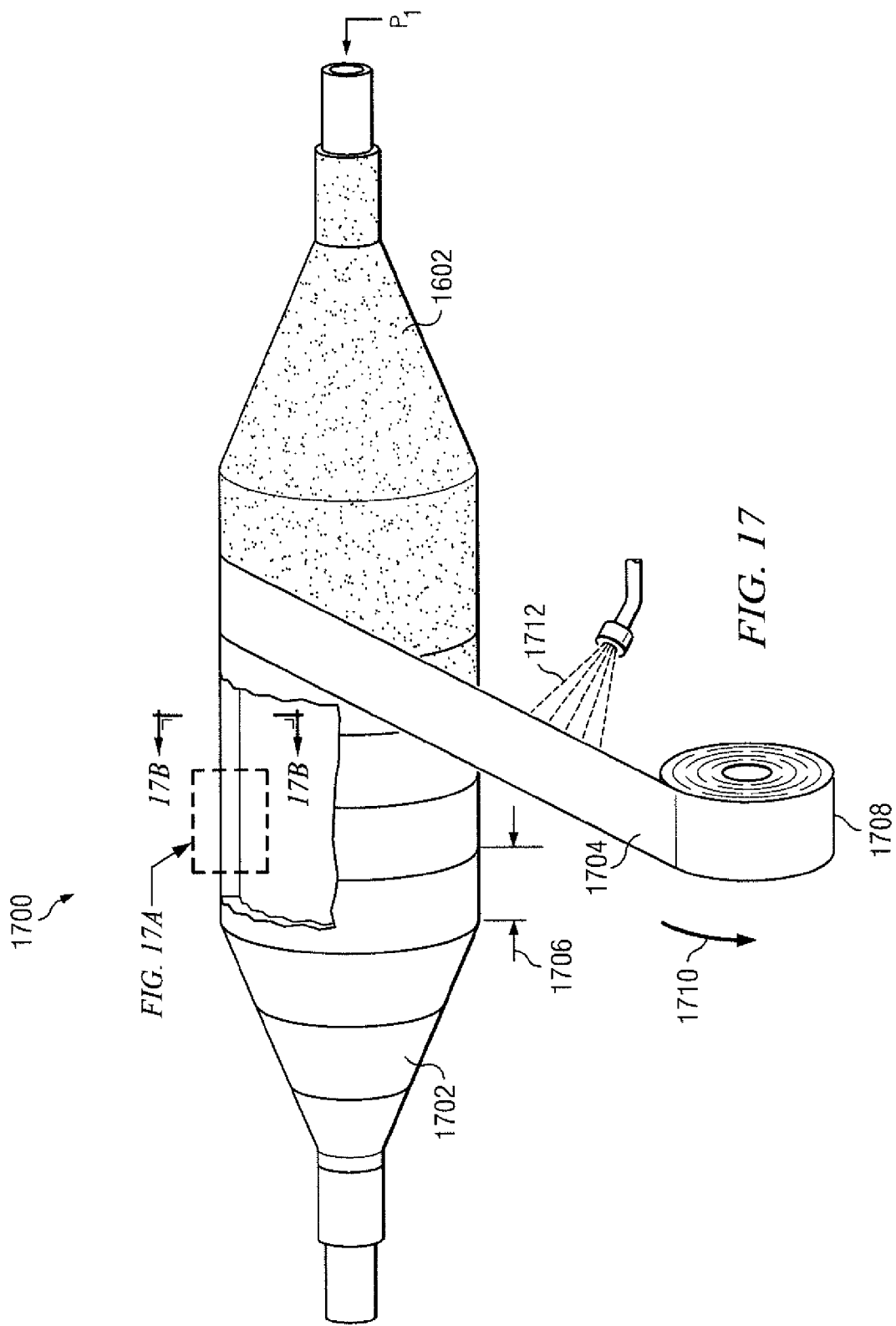
FIG. 17 illustrates wrapping an outer layer over the in-progress balloon and mandrel in accordance with additional embodiments.
Figure 17A:
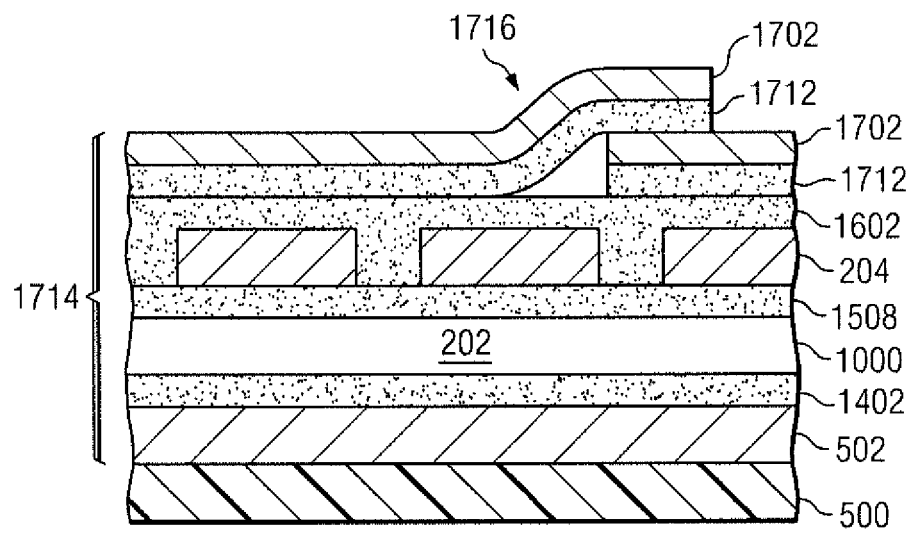
FIG. 17A is an enlarged cross-sectional view of the in-progress balloon wall overlying the mandrel looking in the circumferential direction taken along line 17A-17A of FIG. 17.
Figure 17B:
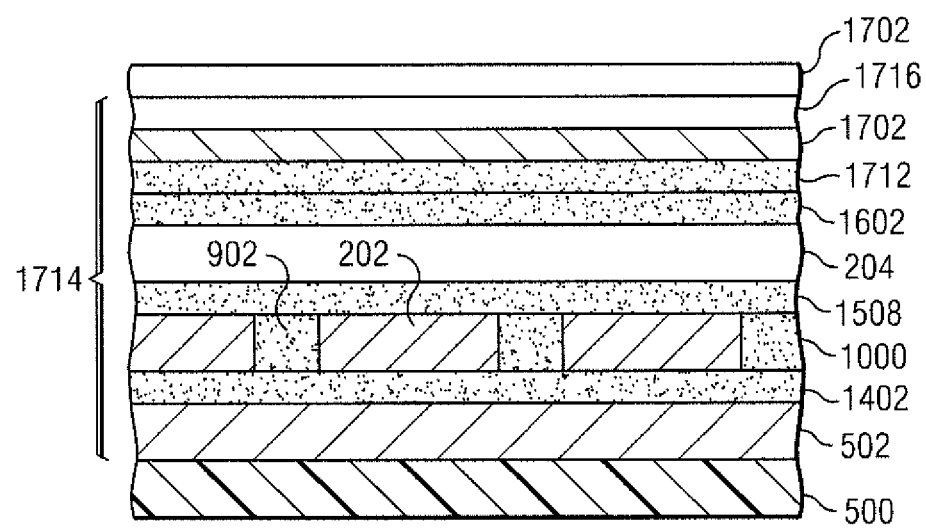
FIG. 17B is an enlarged cross-sectional view of the in-progress balloon wall overlying the mandrel looking in the longitudinal direction taken along line 17B-17B of FIG. 17.

Referring now to FIGS. 17, 17A and 17B, an outer layer 1702 may be affixed over the illustrated balloon lay-up 1700, which now includes the third coating 1602. The balloon lay-up 1700 is supported by the underlying mandrel 500, which remains pressurized at the predetermined internal pressure $P_1$ to maintain its size and shape. The outer layer 1702 may provide additional material to increase the puncture-resistance and surface smoothness of the balloon 100. In some embodiments, the outer layer 1702 may comprise a thermally-weldable polymer material. The outer layer 1702 preferably comprises the same material as the balloon matrix 206 or material compatible with the material of balloon matrix. Preferably the outer layer 1702 is formed from the same material as the conformal layer 502. Thus, when the conformal layer 502 is formed from PEBA thermoplastic elastomer, the outer layer 1702 is preferably formed from the same material. In a preferred embodiment, the outer layer may be formed of PEBA, e.g., Pebax®.

In the illustrated embodiment, the outer layer 1702 may comprise a thermally-weldable polymer tape or film 1704 that may be wrapped circumferentially around the balloon lay-up 1700 at a predetermined pitch 1706. In one embodiment, the pitch 1706 may be smaller than the width of the tape 1704 such that successive winds may overlap. The outer layer tape 1704 may be supplied from a storage drum 1708 or other source. In preferred embodiments, the tape 1704 may be wound continuously around the balloon lay-up 1700 from one neck to the opposite neck. In the illustrated embodiment, the circumferential winding (denoted by arrow 1710) is accomplished by revolving the storage drum 1708 around the balloon lay-up 1700, however in other embodiments the balloon lay-up and mandrel 500 may be rotated. For balloons 100 in the 4 to 12 French Unit size, the outer layer 1702 may be formed of PEBA, e.g., Pebax®, having a thickness of about 0.0003 inches. Such small thickness may be obtained by stretching PEBA tape having an original thickness of about 0.0005 inches.

Prior to affixing the outer layer 1702 onto the balloon lay-up 1700, a fourth coating 1712 of thermally-weldable matrix material may be applied to the underside surface of the outer layer material 1704 to facilitate its retention. The fourth coating 1712 is preferably applied by spraying, but may be applied by brushing, dipping or other means. The fourth coating 1712 will ultimately become the fourth coating region 218 of the matrix 206, therefore it must be compatible for thermal-welding to the other materials in the matrix. In one embodiment, the fourth coating 1712 may be formed of a soluble nylon material having a thickness of about 0.0003 inches. Such a fourth coating 1712 may be thermal-welding compatible with the third coating 1602 when formed of nylon and with the outer layer 1702 when formed of PEBA, e.g., Pebax®. It will be appreciated that the outer layer 1702 may not be welded or permanently joined to the balloon lay-up at this time. It is only necessary that the outer layer 1702 be affixed firmly enough to stay in position during further processing.

Referring now specifically to FIGS. 17A and 17B, after affixing the outer layer 1702, the final lay-up wall 1714 of the balloon 100 is illustrated on the outer surface of the mandrel 500. In the embodiment illustrated, the fourth coating 1712 has been applied as previously described. The overlapping of the tape 1704 is shown at arrow 1716.

Figure 18:
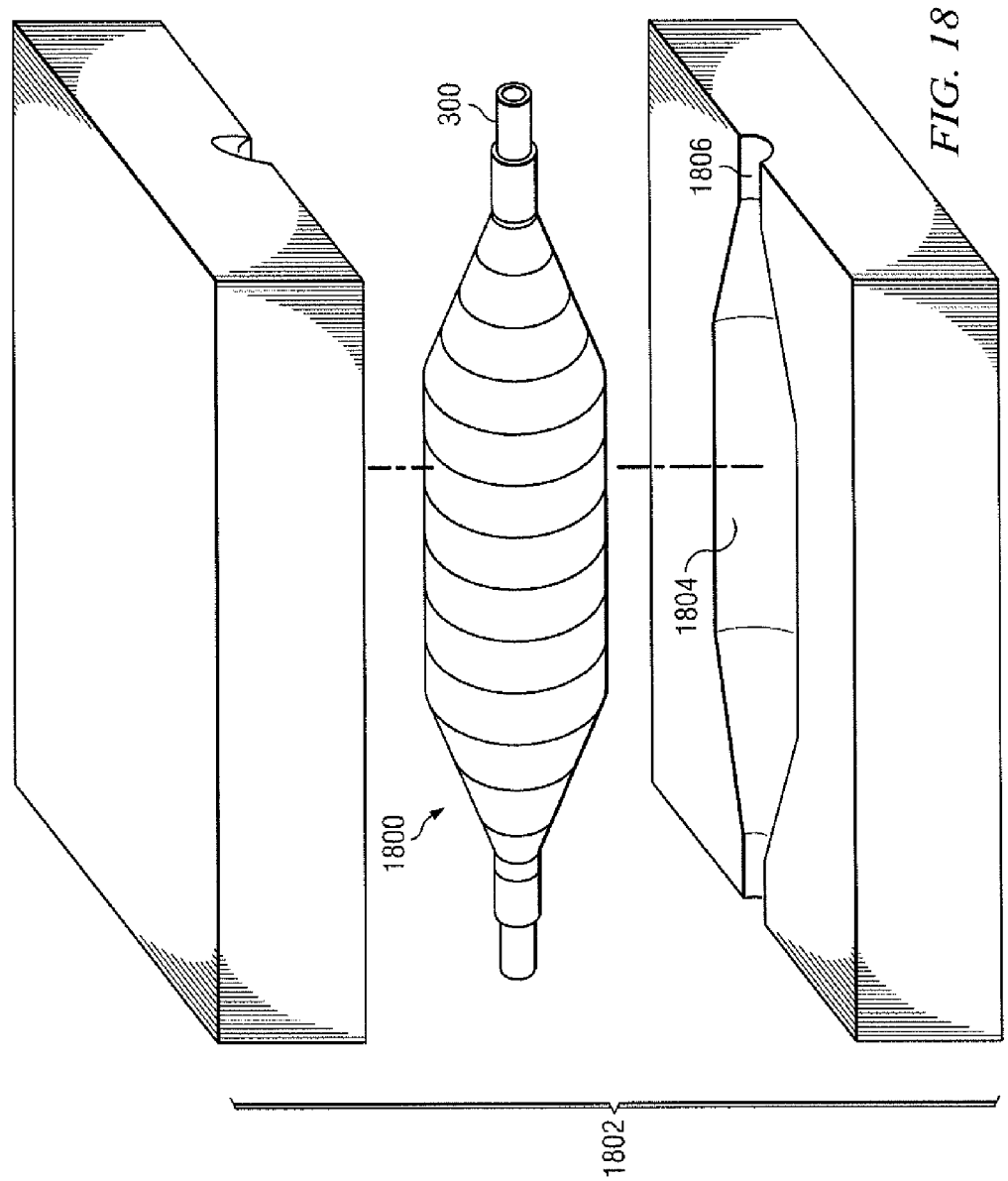
FIG. 18 illustrates placing the final balloon lay-up and mandrel into a die prior to thermal welding in accordance with additional embodiments.
Figure 19:
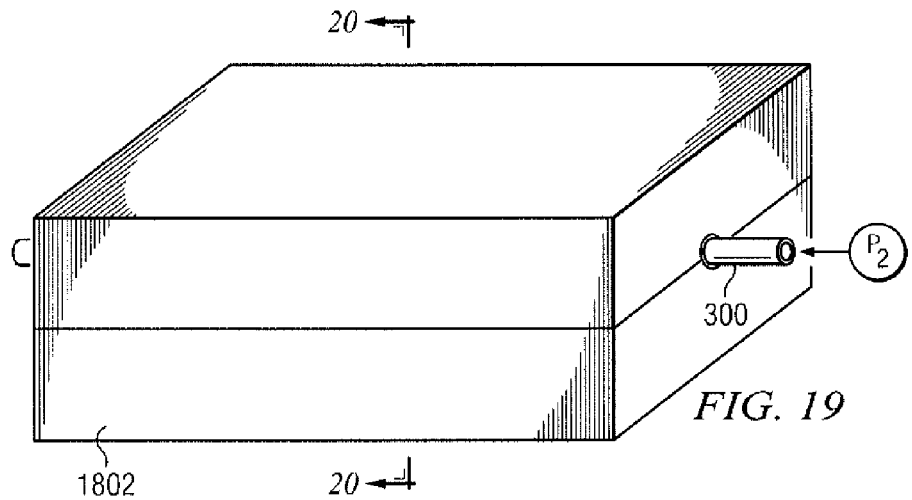
FIG. 19 show the die of FIG. 18 closed over the final balloon lay-up and mandrel prior to thermal welding.
Figure 20:
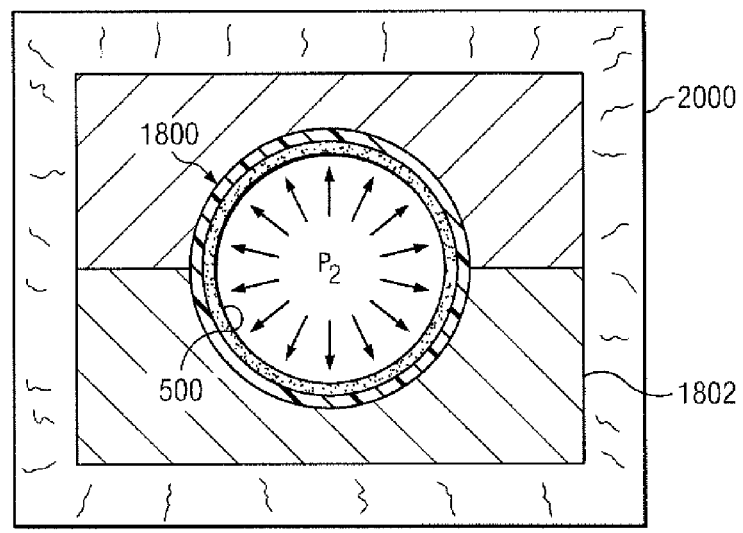
FIG. 20 is a cross-sectional view taken in the direction of line 20-20 of FIG. 19 showing the die, final balloon lay-up and mandrel being heated in a oven in accordance with additional embodiments.

Referring now to FIGS. 18, 19 and 20, there is illustrated the thermal welding of the final balloon lay-up 1800 following application of the outer layer 1702 described above. Referring first to FIG. 18, the final lay-up 1800 (with the mandrel 500 still inside) may be placed inside a die 1802 having a balloon-shaped cavity 1804. Passages 1806 may be provided in die 1802 so that the mandrel tube 300 may extend outside to allow pressurization while the lay-up is in the die.

Referring now to FIG. 19, after the final balloon lay-up 1800 is placed in the die cavity 1804, the die 1802 may be closed and secured. Next, heat and pressure are applied to thermally weld the components of the balloon lay-up into the final balloon 100.

Referring now to FIG. 20, in one embodiment the die 1802 containing the final balloon lay-up 1800 is placed inside an oven 2000 for heating (for purposes of illustration, the wall of the final lay-up 1800 is shown in simplified form in FIG. 20). In other embodiments, a die having integral heating may be used. While inside the die, the mandrel 500 may be internally pressurized to a predetermined pressure $P_2$. Since the mandrel 500 is semi-compliant, the internal pressure $P_2$ will force the mandrel walls outward, pressing each wall 1714 of the final lay-up 1800 against the heated walls of the die cavity 1804. In some embodiments, the die 1802 may be heated before the mandrel 500 is pressurized. In other embodiments, the mandrel 500 may be pressurized before the die 1802 is heated. In still other embodiments, the heating of the die and the pressurization of the mandrel 500 may occur simultaneously. Predetermined conditions of heat and pressure maintained inside the die 1820 for a predetermined time period may weld together the thermally-weldable components of the final lay-up wall 1714 (FIGS. 17A and 17B), thereby forming the finished balloon wall 200 (FIGS. 2A and 2B). In one embodiment, a final balloon lay-up 1800 comprising reinforcing fibers 202, 204 made of Technora® brand para-aramid layered with nylon and Pebax® brand PEBA component layers may be thermally welded by heating the die 1802 to about 300 degrees F., pressurizing the mandrel 500 to about 150 psi, and maintaining these conditions for a period of about 2 minutes.

During the thermal welding process, the thermally-weldable materials in the wall 1714 of the final lay-up 1800 may fuse to one another forming a continuous matrix 206 of the finished balloon wall 200 (FIGS. 2A and 2B). In preferred embodiments, the matrix 206 may be continuous and free of adhesive materials. In some embodiments, the thermally-weldable materials in the wall 1714 of the final lay-up may plastically deform under heat and pressure to fill any voids (e.g., in-between and around the reinforcing fibers) such that the reinforcing fibers 202 and 204 are fully encapsulated by the matrix 206 in the finished balloon 100. In some embodiments, the thermally-weldable materials in the wall 1714 of the final lay-up may plastically deform under heat and pressure to even-out surface irregularities (e.g., the tape overlap 1716) such that the outer surface 230 of the finished balloon wall 200 is very smooth. In some embodiments, the thermally-weldable materials in the wall 1714 of the final lay-up may weld together, plastically deform and/or be compressed under heat and pressure such that the overall thickness of the finished balloon wall 200 is significantly less than the thickness of the wall 1714.

After thermal welding is complete, the die 1802 may be cooled, the pressure in the mandrel 500 may be reduced, and the balloon 100 (still overlying the mandrel 500) may be removed from the die cavity. The walls of the mandrel 500 mandrel walls may then be collapsed by releasing the internal pressure or applying a partial vacuum via the tube 300.

Figure 21:
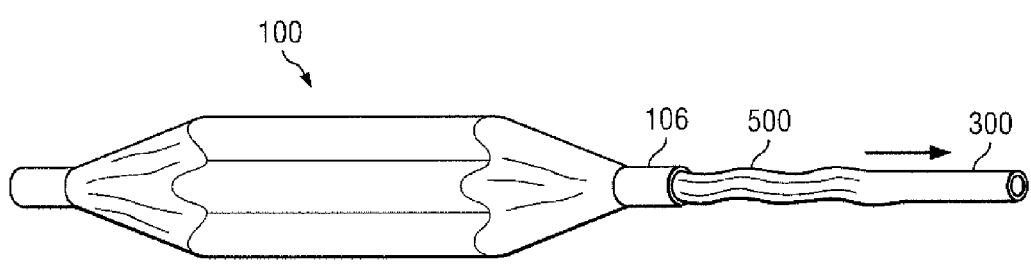
FIG. 21 is a perspective view of the collapsed mandrel being removed from the finished medical balloon after thermal welding in accordance with additional embodiments.

Referring now to FIG. 21, after collapsing the walls of the mandrel 500 inside the balloon 100, the mandrel itself may be removed from the balloon by pulling it through the neck 106 of the balloon by means of tube 300. The balloon 100 is now complete (FIGS. 1 and 2) and ready for inspection and testing or further processing, e.g., attachment to a catheter.

It will be appreciated that the sequence of steps in a method of constructing a medical balloon as disclosed herein may be varied. For example, a first method includes:
 a) preparing a tubular or preformed mandrel (FIGS. 3, 4 and 5C);
 b) coating the mandrel with a solution including a thermally weldable polymer to begin a balloon layup by spraying, dipping or brushing (FIGS. 5H, 5G and 5I) the solution onto the mandrel to begin a balloon layup;
 c) affixing a patterned sock sheet over the coated mandrel (FIG. 14) to form a first fiber layer;
 d) applying a solution including a thermally weldable polymer over the sock sheet by spraying, dipping or brushing the solution over the sock sheet (FIGS. 5H, 5G and 5I);
 e) winding hoop fibers over the sock sheet (FIG. 15) to form a second fiber layer;
 f) applying a solution including a thermally weldable polymer over the sock sheet and hoop fibers by spraying, dipping or brushing (FIGS. 5H, 5G and 5I);
 g) wrapping a film or tape of a thermally weldable polymer material over the sock sheet and hoop fibers (FIG. 17);
 h) heating the layup to weld the thermally weldable polymer materials together to encapsulate the fibers of the sock sheet and hoop fibers in a continuous matrix of the thermally weldable material (FIGS. 18-20); and
 i) removing the mandrel from the balloon (FIG. 21).

A second method of constructing a medical balloon as disclosed herein includes the steps of:
 a) preparing a tubular or preformed mandrel (FIGS. 3, 4 and 5C);
 b) placing a tube of a thermally weldable polymer material over the mandrel (FIG. 4) to begin a balloon layup;
 c) wrapping a film or tape of a thermally weldable polymer material over tube of thermally weldable polymer material (FIG. 5C);
 d) applying a solution including a thermally weldable polymer over the tape or film of weldable polymer material by spraying, dipping or brushing (FIGS. 5H, 5G and 5I);
 e) affixing a patterned sock sheet over the mandrel (FIG. 14) to form a first fiber layer;
 f) applying a solution including a thermally weldable polymer material over the sock sheet by spraying, dipping or brushing (FIGS. 5H, 5G and 5I);
 g) winding hoop fibers over the sock sheet (FIG. 15) to form a second fiber layer;
 h) applying a solution including a thermally weldable polymer material over the sock sheet and hoop fibers by spraying, dipping or brushing (FIGS. 5H, 5G and 5I);
 i) wrapping a film or tape of a thermally weldable material over the sock sheet and hoop fibers (FIG. 17); and
 j) heating the layup to weld the thermally weldable materials together to encapsulate the fibers of the sock sheet and hoop fibers in fibers in a continuous matrix of the thermally weldable material (FIGS. 18-20); and k) removing the mandrel from the balloon (FIG. 21).

A third method of constructing a medical balloon as disclosed herein includes the steps of:
- a) preparing a tubular or preformed mandrel (FIGS. 3, 4 and 5C);
- b) dip coating the mandrel to form a base layer of a thermally weldable polymer material (FIG. 5H) to begin a balloon layup;
- c) applying a solution including a thermally weldable polymer material over the base layer spraying, dipping or brushing (FIGS. 5H, 5G and 5I);
- d) affixing a patterned sock sheet over the mandrel (FIG. 14) to form a first fiber layer;
- e) applying a solution including a thermally weldable polymer material over the sock sheet by spraying, dipping or brushing (FIGS. 5H, 5G and 5I);
- f) winding hoop fibers over the sock sheet (FIG. 15) to form a second fiber layer;
- g) applying a solution including a thermally weldable polymer over the sock sheet by spraying, dipping or brushing (FIGS. 5H, 5G and 5I);
- h) wrapping a film or tape of a thermally weldable polymer material over the sock sheet and hoop fibers (FIG. 17);
- i) heating the layup to weld the thermally weldable polymer materials together to encapsulate the fibers of the sock sheet and hoop fibers in fibers in a continuous matrix of the thermally weldable material (FIGS. 18-20); and
- j) removing the mandrel from the balloon (FIG. 21).

A fourth method of constructing a medical balloon as disclosed herein includes the steps of
- a) preparing a tubular or preformed mandrel (FIGS. 3, 4 and 5C);
- b) dip coating the mandrel in a solution including a thermally weldable polymer material to form a base layer of a thermally weldable material (FIG. 5H);
- c) wrapping a film or tape of a thermally weldable polymer material over the mandrel;
- d) applying a solution including a thermally weldable polymer material over the film or tape by spraying, dipping or brushing (FIGS. 5H, 5G and 5I);
- e) affixing a patterned sock sheet over the mandrel (FIG. 14) to form a first fiber layer;
- f) applying a solution including a thermally weldable polymer material over the sock sheet by spraying, dipping or brushing (FIGS. 5H, 5G and 5I);
- g) winding hoop fibers over the sock sheet (FIG. 15) to form a second fiber layer;
- h) applying a solution including a thermally weldable polymer material over the sock sheet by spraying, dipping or brushing (FIGS. 5H, 5G and 5I);
- i) wrapping a film or tape of a thermally weldable polymer material over the sock sheet and hoop fibers (FIG. 17);
- j) heating the layup to weld the thermally weldable materials together to encapsulate the fibers of the sock sheet and hoop fibers in fibers in a continuous matrix of the thermally weldable material (FIGS. 18-20); and
- k) removing the mandrel from the balloon (FIG. 21).

A fifth method of constructing a medical balloon as disclosed herein includes the steps of:
- a) preparing a tubular or preformed mandrel (FIGS. 3, 4 and 5C);
- b) wrapping the mandrel with one or more, typically two layers of PEBA tape or film (FIG. 17);
- c) spraying or brushing the wrapped mandrel with one or more coats of a weldable polyurethane (e.g. Dow Pellethane®) dissolved in a solvent;
- d) affixing a patterned sock sheet over the coated mandrel (FIG. 14) to form a first fiber layer on the balloon layup;
- e) heating the balloon layup to encapsulate the fibers of the sock sheet in a matrix of the weldable polyurethane (FIGS. 18-20);
- f) winding hoop fibers over the sock sheet (FIG. 15) to form a second fiber layer;
- g) wrapping the layup with one or more layers of PEBA tape or film (FIG. 17);
- h) heating the layup to weld the thermally weldable polymer materials together to encapsulate the fibers of the sock sheet and hoop fibers in a continuous matrix of the thermally weldable material (FIGS. 18-20); and
- i) removing the mandrel from the balloon (FIG. 21).

It will be appreciated that in some embodiments, the above methods may be modified. For example, the recited steps of applying a solution including a thermally weldable polymer material to the balloon lay up at various stages in the processes may, in some cases, be eliminated. Different methods of applying the solution, e.g. dipping, spraying or brushing may be employed to apply the solution. In other embodiments the mandrel used to form the balloon may be coated or wrapped with an adhesion resistant material to facilitate separation of the balloon and mandrel after thermal welding. In other variations, the second fiber layer may be a patterned sock sheet formed from a non-woven, knitted or woven fabric.

It will be appreciated by those skilled in the art having the benefit of this disclosure that this non-compliant medical balloon may provide improved flexibility, simplified assembly, reduced folding wall thickness and/or more uniform wall thicknesses. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

The invention claimed is:

1. A method for forming a medical balloon, comprising:
forming a sheet comprising fibers, wherein the fibers of the sheet comprise fibers of different lengths and are divisible into a first and second group based on length;
affixing the sheet comprising fibers to a mandrel, said fibers being substantially parallel to a longitudinal axis of the mandrel;
providing a thermally weldable polymer material over the mandrel; and
heating the thermally weldable polymer material to encapsulate the fibers of the sheet therein.

2. The method of claim 1, wherein the providing step comprises wrapping the thermally weldable polymer material along the mandrel.

3. The method of claim 1 further comprising after the affixing step, applying a solution including a thermally weldable polymer over the sheet.

4. The method of claim 1, further including the step of winding at least one hoop fiber over the sheet prior to the heating step, and wherein the heating step encapsulates the hoop fiber in the thermally weldable polymer material.

5. The method of claim 4, further including the step of applying a solution including a thermally weldable polymer over the at least one hoop fiber.

6. The method of claim 1, further comprising before the affixing step, at least partially covering the mandrel with a thermally weldable polymer material.

7. The method of claim 1, further comprising before the affixing step, providing a tube of a thermally weldable polymer material on the mandrel.

8. The method of claim 1, further including the step of removing the mandrel after the heating step.

9. The method of claim 1, wherein the forming step comprises fanning the sheet from a pattern of fibers.

10. The method of claim 9, wherein the medical balloon when inflated includes a generally cylindrical barrel wall disposed between tapered cone walls and cylindrical neck walls extending therefrom along a longitudinal axis, and wherein the forming step comprises:
providing a first fiber layer in a pattern, the pattern including a plurality of generally rectangular barrel regions, tapered cone regions on each end of each of the tapered barrel regions; and generally rectangular neck regions extending from each of the tapered cone regions; wherein the tapered cone regions connect the neck regions and barrel regions, and wherein the barrel regions of the pattern are each connected continuously along the length of a side thereof to an adjacent barrel region whereby the first fiber layer defines the generally cylindrical barrel wall, tapered cone walls and cylindrical neck walls when wrapped around the mandrel.

11. A method for use in forming a medical balloon having a barrel wall disposed between tapered cone walls and cylindrical neck walls extending therefrom along a longitudinal axis, the method comprising:
forming a sheet of fibers, wherein the fibers comprise a plurality of fibers of different lengths that are divisible into a first and second group based on length, and wherein a plurality of the fibers are substantially parallel to a longitudinal axis of the balloon; and
thermally welding the sheet of fibers and a polymer material to form at least the barrel wall of the balloon having the fibers embedded in the polymer material.

12. The method of claim 11, further including, before the welding step, applying the polymer material to a mandrel.

13. The method of claim 12, further including the step of removing the mandrel after the welding step.

14. The method of claim 11, further including the step of thermally welding the fibers and polymer material for form the cone walls of the balloon.

15. The method of claim 11, wherein the fibers of the first group extend continuously between and terminate in the neck walls, and the fibers of the second group extend continuously between and terminate in the cone walls.

* * * * *